US011399772B2

(12) United States Patent
Atashbar et al.

(10) Patent No.: US 11,399,772 B2
(45) Date of Patent: Aug. 2, 2022

(54) STETHOGRAPHIC DEVICE

(71) Applicant: The Board of Trustees of Western Michigan University, Kalamazoo, MI (US)

(72) Inventors: Massood Zandi Atashbar, Kalamazoo, MI (US); Binu Baby Narakathu, Portage, MI (US); Xingzhe Zhang, Kalamazoo, MI (US); Dinesh Maddipatla, Kalamazoo, MI (US)

(73) Assignee: The Board of Trustees of Western Michigan University, Kalamazoo, MI (US)

( * ) Notice: Subject to any disclaimer, the term of this patent is extended or adjusted under 35 U.S.C. 154(b) by 502 days.

(21) Appl. No.: 16/369,751

(22) Filed: Mar. 29, 2019

(65) Prior Publication Data

US 2019/0298269 A1    Oct. 3, 2019

Related U.S. Application Data

(60) Provisional application No. 62/650,781, filed on Mar. 30, 2018.

(51) Int. Cl.
*A61B 5/00* (2006.01)
*A61B 7/00* (2006.01)
(Continued)

(52) U.S. Cl.
CPC ............ *A61B 5/7225* (2013.01); *A61B 5/002* (2013.01); *A61B 5/0205* (2013.01);
(Continued)

(58) Field of Classification Search
CPC ....... A61B 5/7225; A61B 5/002; A61B 5/742; A61B 7/003; A61B 5/0205; A61B 5/7228; A61B 5/7282; A61B 5/0816; A61B 5/0245; A61B 7/02; H04Q 9/00; H04Q 2209/40; G10L 25/66; G16H 40/63; G16H 10/60; G16H 50/20
See application file for complete search history.

(56) References Cited

U.S. PATENT DOCUMENTS 3,990,435 A   11/1976   Murphy
5,165,417 A   11/1992   Murphy, Jr.
(Continued)

OTHER PUBLICATIONS

Wong, "Design, Characterization and Application of a Multiple Input Stethoscope Apparatus," A Thesis Presented to the Faculty of California Polytechnic State University, San Luis Obispo, Sep. 2014 (170 pages).

(Continued)

*Primary Examiner* — Devin B Henson
*Assistant Examiner* — Joseph A Tombers
(74) *Attorney, Agent, or Firm* — Price Heneveld LLP

(57) ABSTRACT

A multichannel stethographic device includes a plurality of individual stethoscopes that may be embedded in a foam pad or surface mounted on a thin flexible substrate. Additional stethoscopes for the heart and thorax may also be utilized. The system may include a signal conditioning circuit, wireless DAQ module, and software (algorithms). The systems may be configured to identify and diagnose various disease conditions such as pneumonia, chronic obstructive pulmonary disease (COPD), asthma, congestive heart failure (CHF), interstitial pulmonary fibrosis (IPF), and vocal cord dysfunction (VCD).

20 Claims, 21 Drawing Sheets

(51) Int. Cl.
  *A61B 5/0205* (2006.01)
  *H04Q 9/00* (2006.01)
  *G10L 25/66* (2013.01)
  *G16H 40/63* (2018.01)
  *A61B 5/08* (2006.01)
  *A61B 5/0245* (2006.01)

(52) U.S. Cl.
  CPC .......... *A61B 5/7228* (2013.01); *A61B 5/7282* (2013.01); *A61B 5/742* (2013.01); *A61B 7/003* (2013.01); *G10L 25/66* (2013.01); *G16H 40/63* (2018.01); *H04Q 9/00* (2013.01); *A61B 5/0245* (2013.01); *A61B 5/0816* (2013.01); *H04Q 2209/40* (2013.01)

(56) References Cited

U.S. PATENT DOCUMENTS

| | | |
|---|---|---|
| 5,844,997 A | 12/1998 | Murphy, Jr. |
| 6,139,505 A | 10/2000 | Murphy |
| 6,699,204 B1 | 3/2004 | Kehyayan et al. |
| 7,520,861 B2 | 4/2009 | Murphy |
| 8,920,343 B2 | 12/2014 | Sabatino |

OTHER PUBLICATIONS

Messner et al., "Respiratory Airflow Estimation from Lung Sounds Based on Regression," IEEE in Acoustics, Speech and Signal Processing Conf. Proceedings, Jun. 2017, pp. 1123-1127 (5 pages).
Peng et al., "High Sensitivity Capacitive Pressure Sensor With Bi-Layer Porous Structure Elastomeric Dielectric Formed by a Facile Solution Based Process," IEEE Sensors Letters vol. 3, No. 2, Feb. 2019 (4 pages).

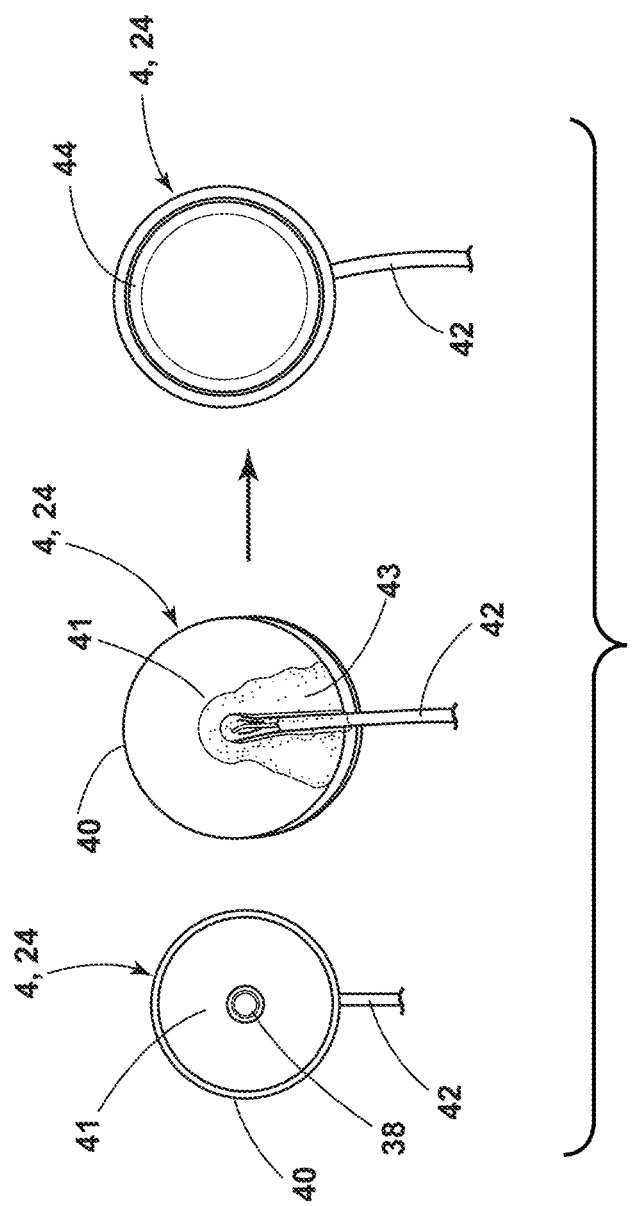

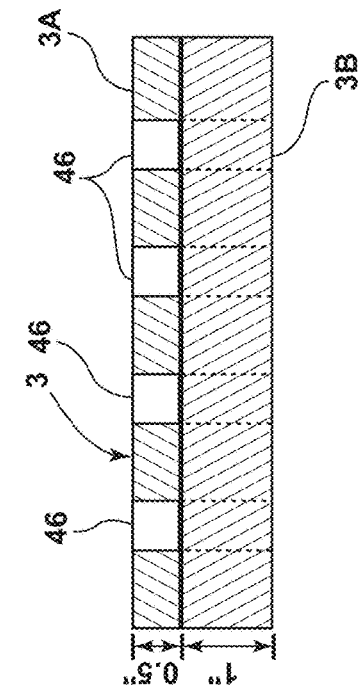
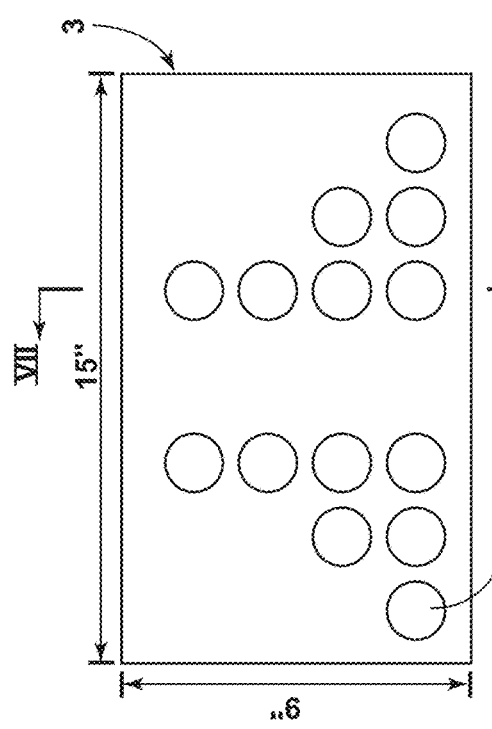
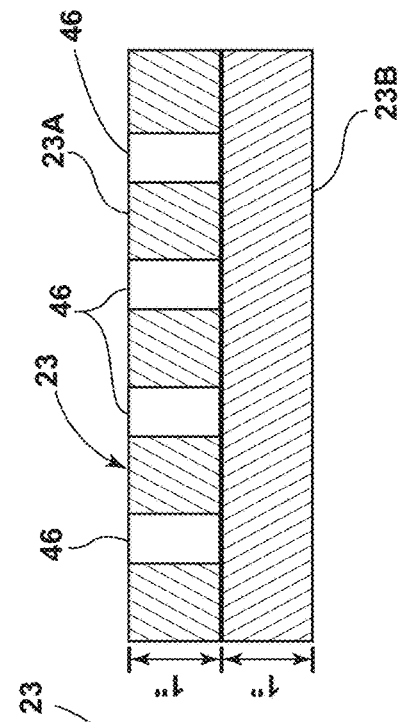
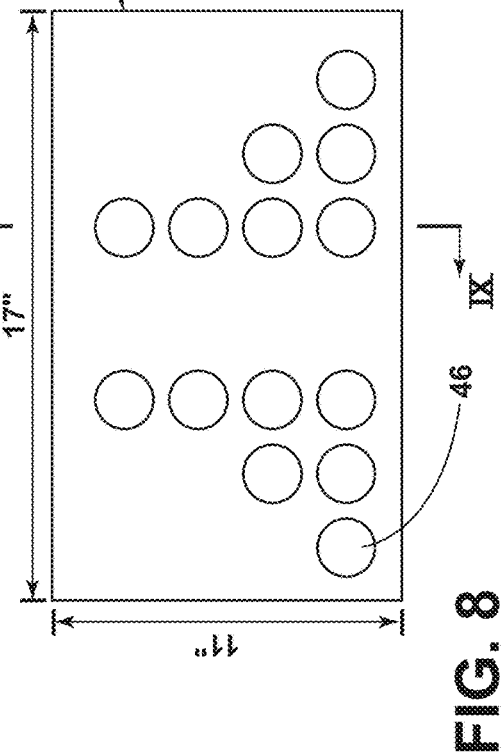

STETHOGRAPHIC DEVICE

CROSS-REFERENCE TO RELATED APPLICATION

This application claims the benefit under 35 U.S.C. § 119(e) of U.S. Provisional Patent Application No. 62/650,781, filed Mar. 30, 2018, entitled "STETHOGRAPHIC DEVICE," which is incorporated herein by reference in its entirety.

BACKGROUND OF THE DISCLOSURE

Stethoscopes may be used to obtain acoustic information from the chest of a patient to facilitate diagnosis of various conditions.

Several categories of heart and lung sounds may be detected and classified utilizing a stethoscope. For example, clinicians may listen to lung sounds using a stethoscope. However, this process may be subject to a variety of limitations. In an effort to overcome limitations associated with stethoscopes, research has been conducted in an effort to develop computerized systems to record heart and lung sounds for various cardiovascular diseases (CD) analysis.

Computerized systems for recording either lung sounds or heart sounds are known. For example, a multichannel lung sound recording device is described in E. Messner, M. Hagmüller, P. Swatek, F. M. Smolle-Jüttner, and F. Pernkopf, "Respiratory airflow estimation from lung sounds based on regression", IEEE in Acoustics, Speech and Signal Processing Conf. Proceedings, pp. 1123-1127, 2017.

Known recording devices may include a commercially available pre-amplifier device with an integrated ADAT interface that is commonly used for computer audio systems, stand-alone hard disk recorders, and/or analog or digital workstations.

A multi-channel computerized heart sound recording apparatus has also been developed (See S. G. Wong, "Design, Characterization and Application of a Multiple Input Stethoscope Apparatus", Master thesis, California Polytechnic State University, San Luis Obispo, 2014.) The recording apparatus uses a commercially available signal conditioning device which is a fixed-gain microphone amplifier.

However, known devices and processes may suffer from various drawbacks.

SUMMARY OF THE DISCLOSURE

One aspect of the present disclosure is a multi-channel stethograph system including a signal conditioning circuit providing both variable gain and Wi-Fi communication. The multi-channel stethograph system provides more advanced diagnostic and monitoring capability with respect to heart and lung sounds with high precision. The multi-channel stethograph system of the present disclosure may overcome various limitations of prior systems.

Another aspect of the present disclosure is a method of diagnosing heart and lung diseases of a patient. The method includes utilizing a plurality of stethoscopes to generate a plurality of audio data sets corresponding to each stethoscope. The audio data sets comprise a) at least one data set generated by a heart stethoscope positioned on the patient to generate a heart audio data set; b) at least one trachea data set generated by a trachea stethoscope positioned on the patient to generate a trachea audio data set; and c) a plurality of lung data sets generated by a plurality of lung stethoscopes positioned on the patient. The method may further include utilizing a computing device to extract features comprising respiratory rates, inspiration and expiration from the trachea data set, utilizing a computing device to extract features comprising heartbeat rate and abnormal heartbeat patterns from the heart data set, and utilizing a computing device to extract features comprising wheeze, rhonchi, squawk, coarse crackle and fine crackle and corresponding frequencies from the lung data sets. The method may further include causing a computing device to utilize predefined disease criteria and the extracted features to determine a result, wherein the result comprises at least one of COPD, asthma, VCD, pneumonia, CHF, and IPF.

These and other features, advantages, and objects of the present disclosure will be further understood and appreciated by those skilled in the art by reference to the following specification, claims, and appended drawings.

BRIEF DESCRIPTION OF THE DRAWINGS

In the drawings:

FIG. 5 is a partially fragmentary perspective view of a stethoscope according to an aspect of the present disclosure;

FIG. 6 is a schematic top plan view of a foam pad according to an aspect of the present disclosure;

FIG. 7 is a schematic side elevational view of the foam pad of FIG. 6;

FIG. 8 is a schematic top plan view of a foam pad according to another aspect of the present disclosure;

FIG. 9 is a schematic side elevational view of the foam pad of FIG. 8;

DETAILED DESCRIPTION

Figure 1:
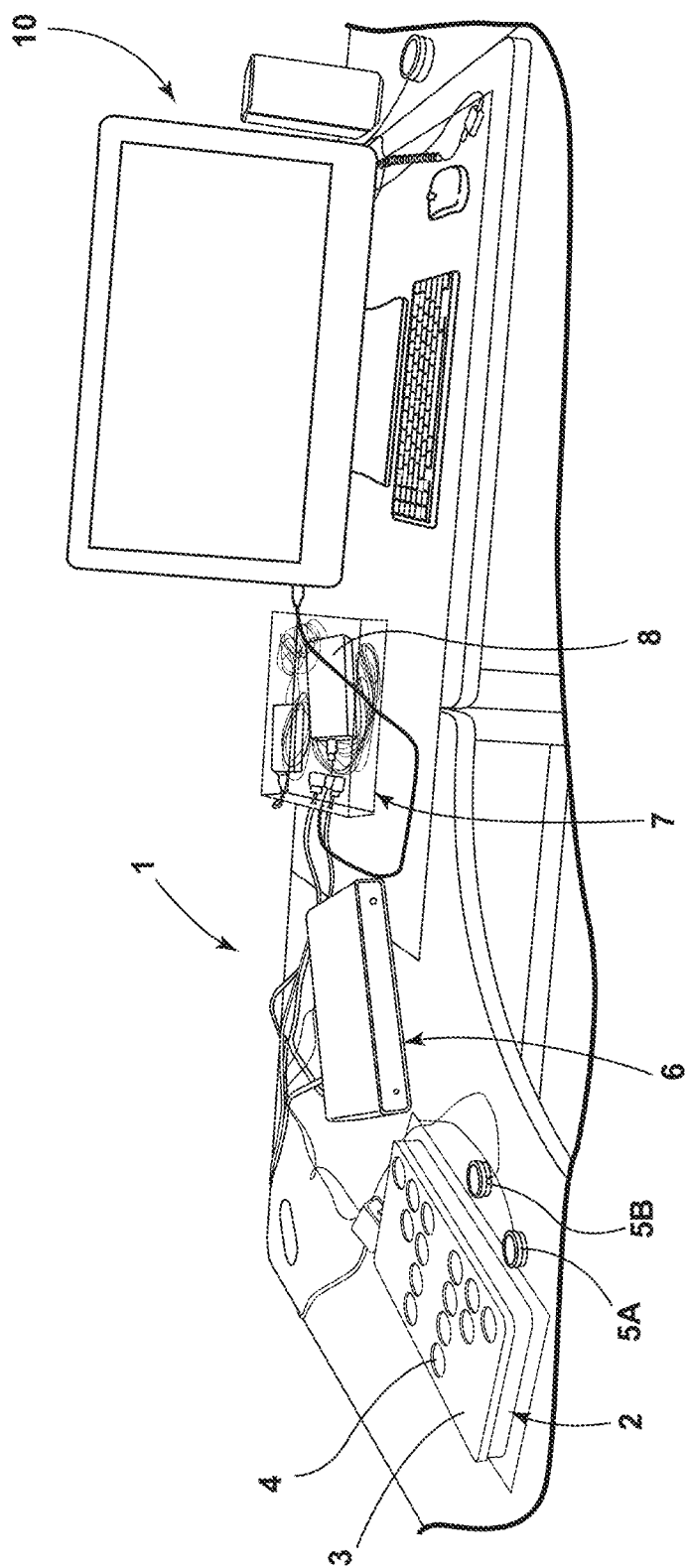
FIG. 1 is a partially fragmentary perspective view of a wireless stethograph system according to one aspect of the present disclosure.

For purposes of description herein, the terms "upper," "lower," "right," "left," "rear," "front," "vertical," "horizontal," and derivatives thereof shall relate to the disclosure as oriented in FIG. 1. However, it is to be understood that the invention may assume various alternative orientations and step sequences, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

FIG. 1 shows a 16-channel wireless stethograph system 1 according to one aspect of the present disclosure. Each of the 16 channels corresponds to data collected by fourteen stethoscopes. Wireless stethograph system 1 is capable of acquiring acoustic sounds from a patient's lung, trachea and heart, and simultaneously converting the sounds to an electrical signal. As discussed below, system 1 also includes noise filtering capabilities.

Figure 2:
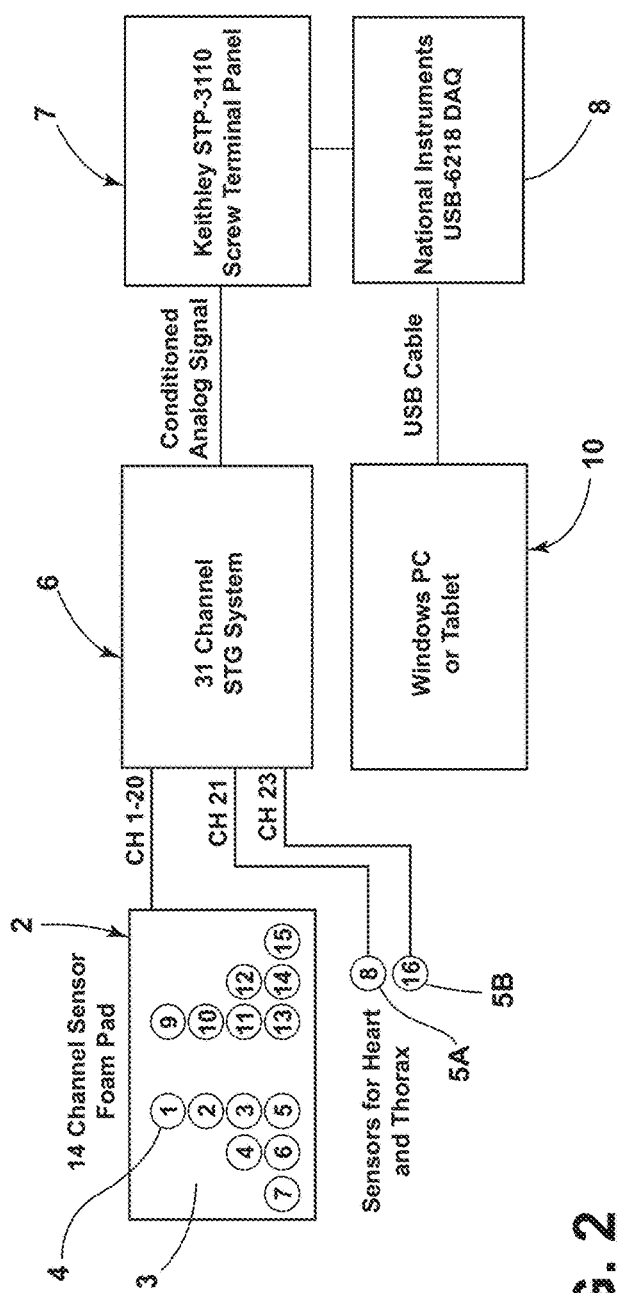
FIG. 2 is a schematic drawing of the components of the wireless stethograph system of FIG. 1.

With reference to FIGS. 1 and 2, the wireless stethograph system 1 includes a sensor assembly 2 comprising a memory foam padding 3 with fourteen stethoscopes 4, two additional stethoscopes 5A and 5B for heart and thorax, a signal conditioning box 6, a screw terminal panel 7, a DAQ 8, and a standard PC 10 configured to execute software developed by Stethographics, Inc. of Boston, Mass.

As discussed in more detail below in connection with FIG. 5, the stethoscopes 4, 5A, 5B may be fabricated by placing microphone-based transducers 38 in a polymer casing 40 with a diaphragm 44. As shown in FIGS. 6 and 8, fourteen stethoscopes 4 may be positioned in the memory foam padding 3 to thereby position stethoscopes 4 at predefined chest cavity locations (over the posterior chest and lateral bases). This placement/positioning enables accurate sensing/acquisition of lung sounds. A first external stethoscope 5A may be placed on an area of a patient near the patient's heart to sense heart sounds. A second external stethoscope 5B may be on the side of a patient's wind pipe to monitor tracheal sounds. Signal conditioning box 6 may be used to reduce noise and to amplify electrical signals acquired from the stethoscopes 4, 5A, 5B. The data acquisition (DAQ) system 8 may be used to acquire the amplified analog signals from the signal conditioning box 6 through screw terminal panel 7. The analog signals are then converted to digital signals. The digital signals may be recorded and analyzed using a computer 10 running software to detect/identify any disorders in the lungs and heart. In a preferred embodiment, the digital signals have a signal to noise ratio (SNR) of at least about 7.3 dB. This software is available from Stethographics, Inc. of Boston Mass. It will be understood that the number and position of stethoscopes 4 may be adjusted or varied as required for a particular application, and the present disclosure is not limited to any specific number of stethoscopes 4, positions of stethoscopes 4, etc.

Figure 3:
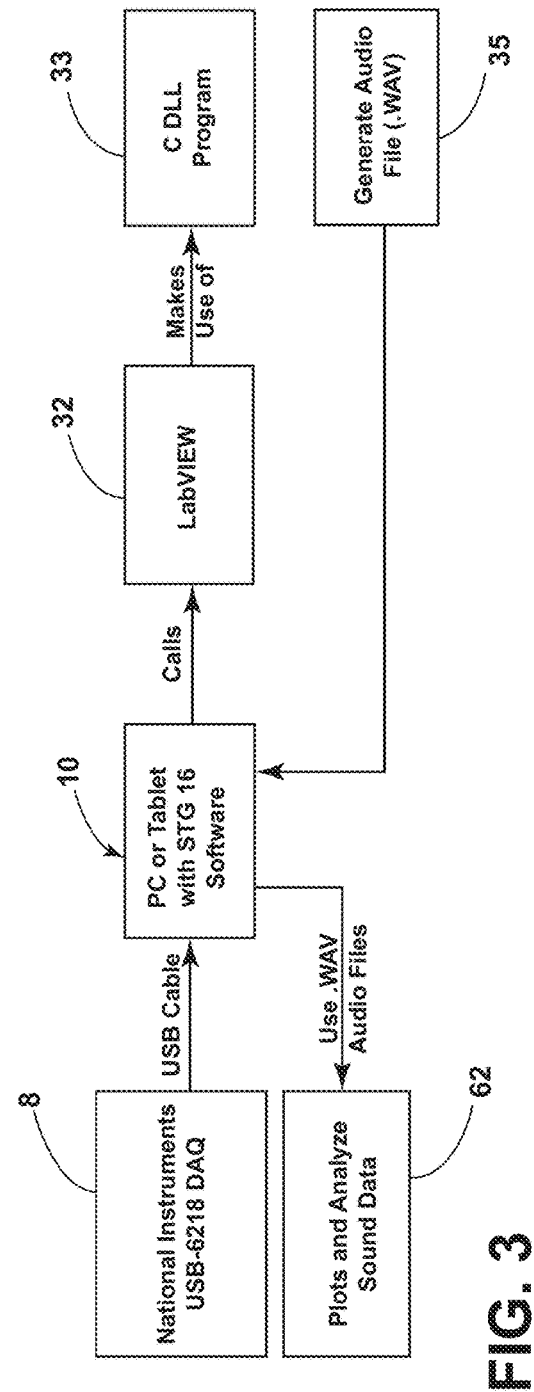
FIG. 3 is a schematic drawing of software data flow of the wireless stethograph system of FIG. 1.

An experimental setup of a system 1 is shown schematically in FIG. 2, and data flow of the software of system 1 is shown schematically in FIG. 3. Digital data from DAQ 8 is transferred to computer 10 via a USB cable 12. In use, the software program ("STG 16") of computer 10 launches a LabVIEW VI program 32 (FIG. 3) which configures the DAQ 8 and records a data sample (e.g. 20 seconds) for each channel/stethoscope. The LabVIEW VI program 32 also converts the channel buffers to .WAV file format at 35 using a 'C' DLL program 33. Then, the program opens the .WAV files directly and reads in the .WAV files, to plot and analyze the sound data at 62.

Figure 4:
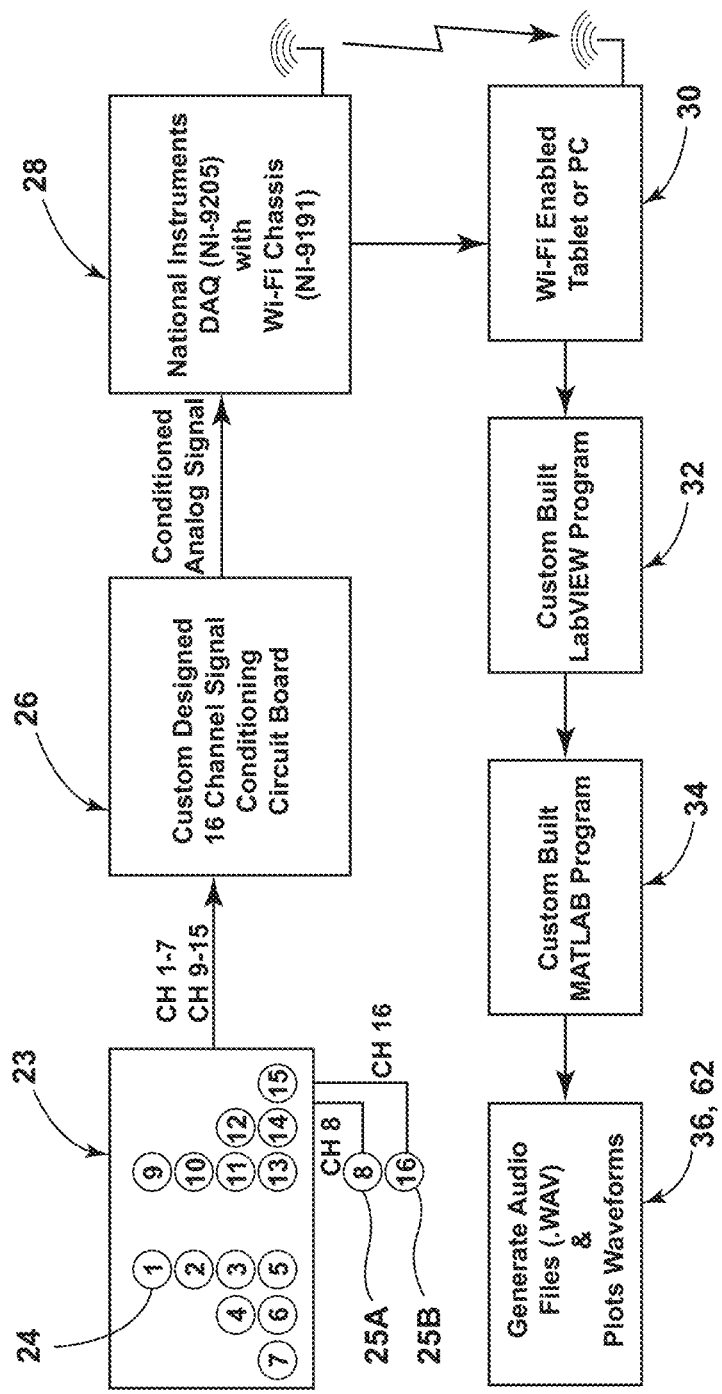
FIG. 4 is a schematic drawing showing a multi-channel stethograph system according to another aspect of the present disclosure.

A second multi-channel stethograph system 20 according to another aspect of the present disclosure is shown schematically in FIG. 4. The multi-channel stethograph system 20 includes a high-density memory foam pad 23 embedded with fourteen stethoscopes 24, a 16-channel signal conditioning system 26, DAQ 28 with Wi-Fi chassis, and a Wi-Fi enabled computer 30 (e.g. a PC or tablet) with LabVIEW® program. External stethoscopes 25A, 25B may be utilized for the heart and thorax. Stethoscopes 4, 5A, 5B, 24, 25A, 25B may have substantially identical construction.

With reference to FIG. 5, a stethoscopes 24 for stethoscope systems 10 and/or 20 may be fabricated by placing microphone based transducers 38 in a through-hole 41 of a disk-shaped casing 40. Casing 40 may be formed by machining a polymer (e.g. Delrin®) material. The casings/disks 40 have a height of 0.5 inches and a radius of 0.875 inch. A wire 42 from transducer 38 is disposed in a groove 43 formed in disk 40. Transducer 38 is covered by a 3M Littmann diaphragm 44. Fourteen stethoscopes 24 are positioned in a high-density memory foam pad 23 (FIG. 4). The high-density memory foam pad 23 provides good contact with a patient's chest wall. Foam pad 23 also provides comfort to the patient and conforms to the patient's body contour when lying/leaning on the pad 23. Still further, pad 23 also provides acoustic isolation from stethoscope-to-stethoscope.

In use, the stethoscopes are placed directly on the heart and trachea areas to acquire sounds simultaneously from the lung, heart and trachea. The lungs, heart and trachea sounds are very small in amplitude and produce very small electrical signals from the stethoscopes (<100 mV). This may create difficulties with respect to direct analysis of the sound characteristics. The sounds (electrical signals) acquired from the sixteen stethoscopes 24, 25A, 25B are processed (noise reduction and amplification) through a 16-channel signal conditioning PCB 26. A National Instruments (NI) data acquisition system (DAQ) 28 may be used to acquire and convert the conditioned signal from the PCB 26 to a digital signal. An NI wireless module of DAQ 28 is used to wirelessly transmit the digital data to a Wi-Fi enabled computer 30 (e.g. a PC or tablet). A custom LabVIEW program 32 records/stores the digital data from the DAQ 28. A MATLAB program 34 converts the recorded data from the stethoscopes 24, 25A, 25B into 16 audio files (for audio playback) and plots the audio waveforms in time domain for visual examination.

Examples of waveforms displayed on a screen of computer 30 via graphical user interfaces (GUIs) are discussed below in connection with FIGS. 16-19. Visual examination of the audio waveforms can be used to identify abnormal patterns in breathing (inspiration and expiration). This provides information on any wheezes, crackles and rhonchi sounds which helps in analyzing the condition of the heart and the lungs. The audio waveforms are displayed in a time expanded mode and provide objective evidence to assist physicians with respect to clinical diagnosis and monitoring of lung and heart disorders, particularly chronic obstructive pulmonary disease (COPD), asthma, pneumonia, and congestive heart failure.

Foam pads 3, 23 (FIGS. 6-9) may comprise high density memory foam having 5.3 lbs/Cubic ft density with indentation force deflection (IFD) of 9-10 lbs/50 sq. inch. High-density memory foam provides better compression rates and longer life compared to medium and low-density memory foams. Top and bottom memory foam pads 3A and 3B respectively of foam pad 3 (FIGS. 6, 7) are 15 inch in length and 9 inch in width, and have 0.5 inch and 1 inch thickness, respectively. The top and bottom memory foam pads 23A and 23B of pad 23 (FIGS. 8, 9) are 17 inch in length and 11 inch in width with a thickness of 1 inch each.

Figure 10:
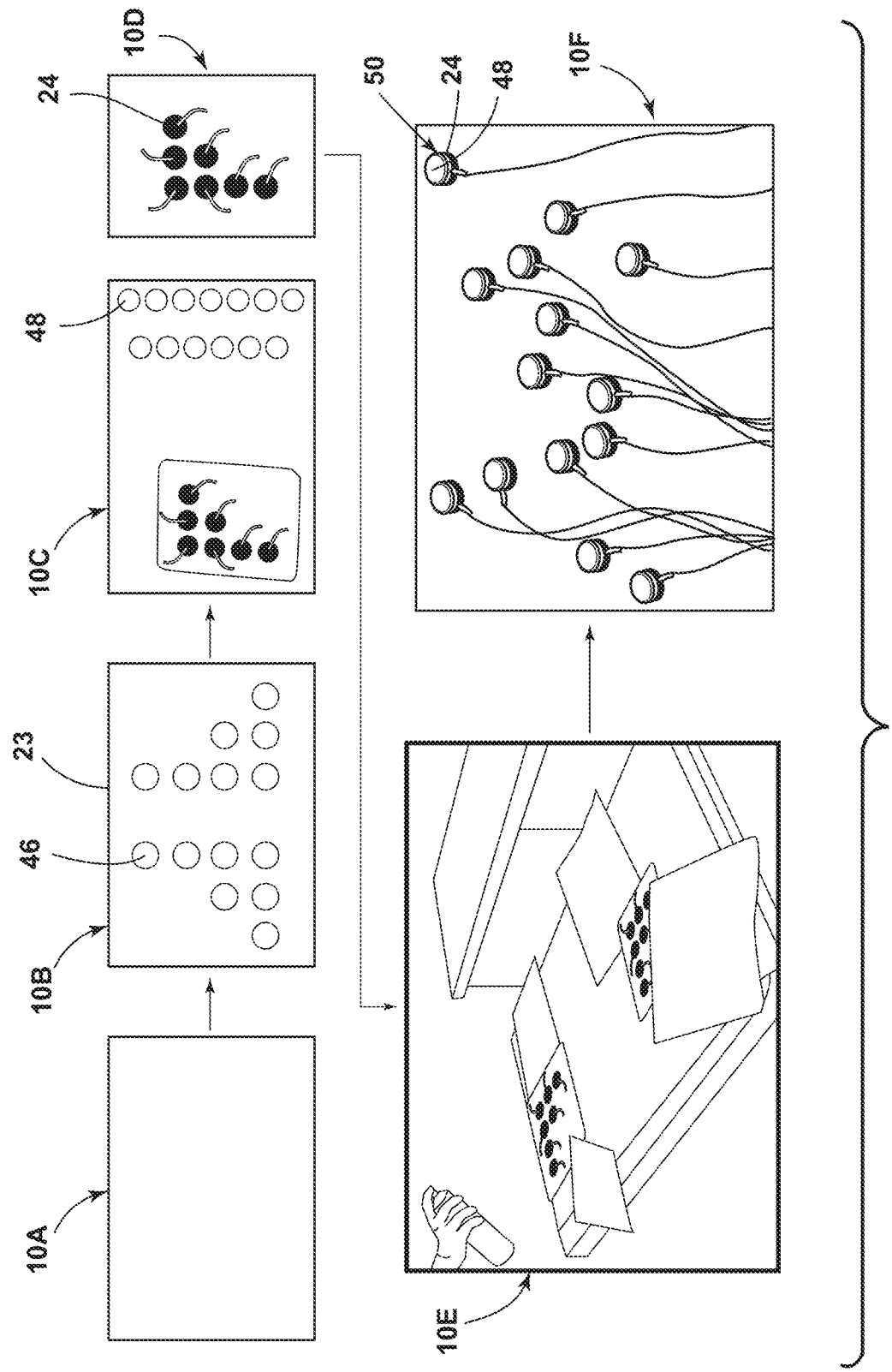
FIG. 10 is a partially schematic flowchart showing production of a foam pad with stethoscopes according to an aspect of the present disclosure.

With reference to FIG. 10, at steps 10A and 10B, 40 mm holes 46 were formed (e.g. punched out) in the top memory foam pad layers 3A, 23A to embed the stethoscopes. At step 10C, the punched-out pieces from the foam pad were sliced horizontally in half (0.5 inch thick). These cut pieces 48 are then attached to the bottom of the stethoscopes 24 to hold the stethoscopes 24 in place without being pushed into the foam pad 3, 23 when placed behind the patient's chest. To attach the cut pieces 48 to the stethoscopes, a dummy memory foam pad with punched out holes was made. The stethoscopes 24 were inserted into the dummy foam pad holes and the punched-out memory foam pieces were attached to the stethoscopes 24 using a spray adhesive as shown at step 10E. The dummy foam pad protects the sides and top part of the casings/disks 40 from being exposed to the spray adhesive. The stethoscopes 24 were glued to the punched-out foam pieces 48 to form assemblies 50 as shown at step 10F.

Then, the assemblies 50 comprising stethoscopes 24 glued to the foam pieces 48 were embedded into the top memory foam pad layer (3A or 23A). In order to relieve stress on the stethoscope wires, superficial cuts were made in the memory foam pad, and the top and bottom layers 3A, 3B and 23A, 23B are adhered together utilizing spray adhesive.

Figure 11:
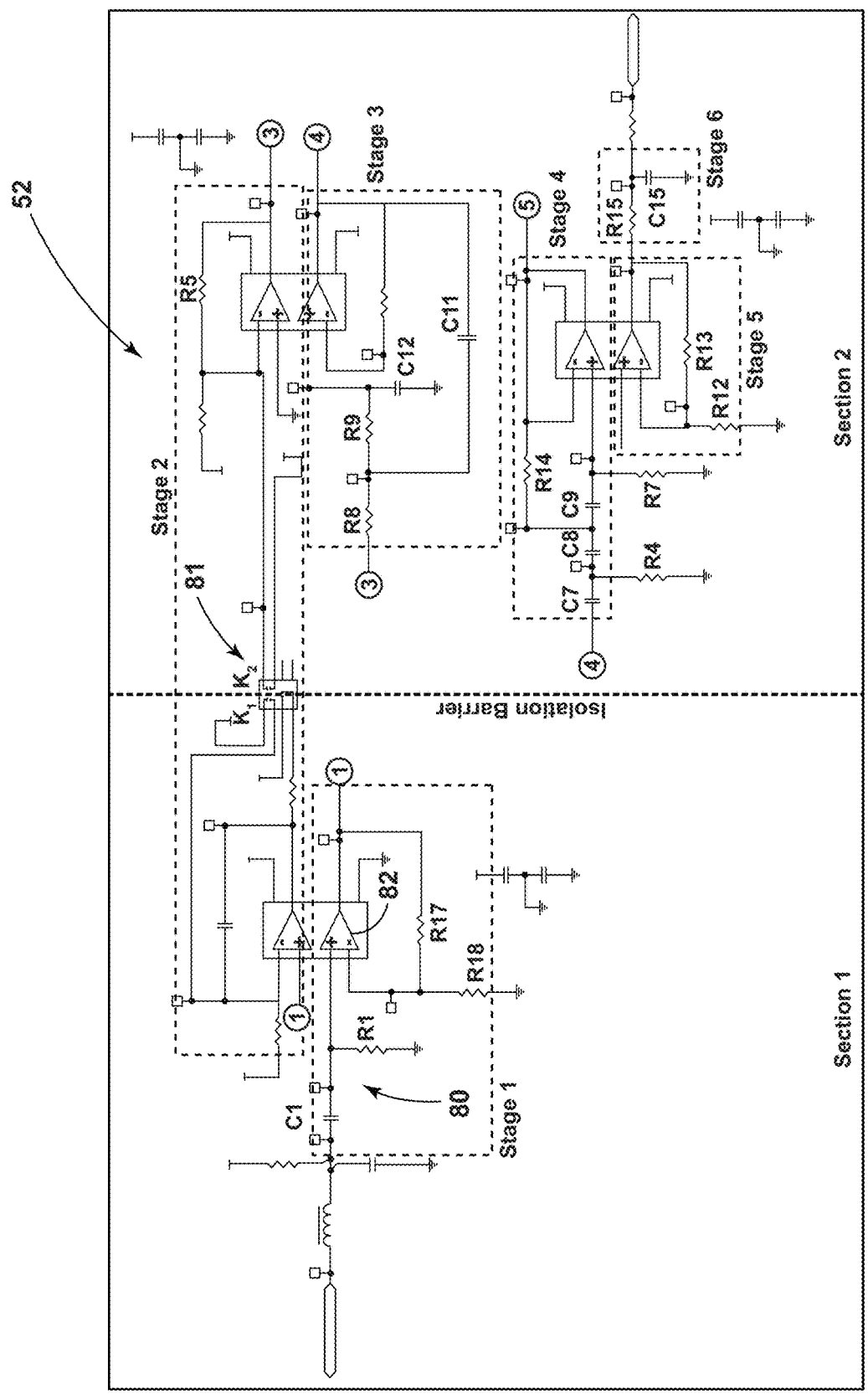
FIG. 11 is a circuit diagram showing a signal conditioning circuit according to one aspect of the present disclosure.

The electrical signals generated by the stethoscopes are 24, 25A, 25B in response to noise comprise small voltages (<100 mV) that are prone to external noise such as body noises, ambient/background noises, etc. These signals therefore might benefit from signal conditioning for further analysis. To address this issue, a signal conditioning circuit 52 (FIG. 11) may be used to reduce the noise level in the electrical signal and amplify it for further analysis such as analog-to-digital (A/D) conversion or to plot the waveforms.

Signal conditioning circuit 52 was designed with a gain of 24 with an operating frequency range from about 50 Hz to about 1600 Hz. Various components such as capacitors, resistors, and IC chips were used for building filters and amplifiers, and a linear optocoupler 81 (which may be, for example, part no. IL300-DEPO from Vishay) were used as isolators. In addition to this, two power supply circuit designs: power circuit_1 (FIG. 12) and power circuit_2 (FIG. 13) were used for generating specific voltages to power the signal conditioning circuit for Section 1 and Section 2, respectively.

The signal conditioning circuit is divided into 6 stages with each stage performing a particular function. Stage 1 is a second order high pass filter powered by power circuit_1 and it includes a passive high pass filter 80 with cut-off frequency of 2.3 Hz (for blocking the DC) (Eq. (1)) and a non-inverting amplifier 82 (to amplify the input AC signal from stethoscope) with a gain of 6 calculated using Eq. (2):

$$\text{Frequency} = \frac{1}{2\pi \cdot R1 \cdot C1} = 2.3 \text{ Hz} \tag{1}$$

$$\text{Gain} = 1 + \frac{R17}{R18} = 6 \tag{2}$$

Stage 2 functions as an isolator amplifier (powered by power circuit_1 and power circuit_2) and isolates the DC voltage from power circuit_1. It allows only the AC signal from stage 1 and amplifies this signal with a gain of 1.14, calculated based on the Eq. (3):

$$\text{Gain} = \frac{K2 \cdot R5}{K1 \cdot R20} = 1.14 \tag{3}$$

Stage 3 is a second order active low pass filter with a cut-off frequency of 1600 Hz, calculated using Eq. (4). The signal frequencies (from stage 2) that are greater than 1600 Hz are considered to be interference sounds and are filtered in order to reduce the noise. Stage 3 is powered by power circuit_2.

$$\text{Frequency} = \frac{1}{2\pi \sqrt[2]{C11 \cdot C12 \cdot C8 \cdot R9}} = 1600 \text{ Hz} \tag{4}$$

Stage 4 is a third-order active high pass filter with a cut-off frequency at 50 Hz, calculated using Eq. (5), and powered by power circuit_2. The signal frequencies from stage 3 that are lower than 50 Hz are considered as noises and are filtered.

$$\text{Frequency} = \frac{1}{2\pi \sqrt[3]{C7 \cdot C8 \cdot C9 \cdot R4 \cdot R7 \cdot R14}} = 50 \text{ Hz} \tag{5}$$

Stage 5 is a non-inverting amplifier and amplifies the signal from stage 4 with a gain of 3.5 and is powered by powered by power circuit_2.

$$\text{Gain} = 1 + \frac{R13}{R12} = 3.5 \qquad (6)$$

The stage 6 is a first order passive low pass filter with cut-off frequency at 1600 Hz, calculated using Eq. (7), and is powered by powered by power circuit_2.

$$\text{Frequency} = \frac{1}{2\pi \cdot R15 \cdot C15} = 1600 \text{ Hz} \qquad (7)$$

In summary, stage 1, stage 3, stage 4 and stage 6 together function as a band pass filter with frequency range from 50 Hz to 1600 Hz.

During testing of circuit 52, a 200 mV AC signal was supplied to the input of 50 Hz frequency and an output signal of 4.9 V AC at 50 Hz was observed on a digital oscilloscope with a gain of 24.5.

Figure 12:
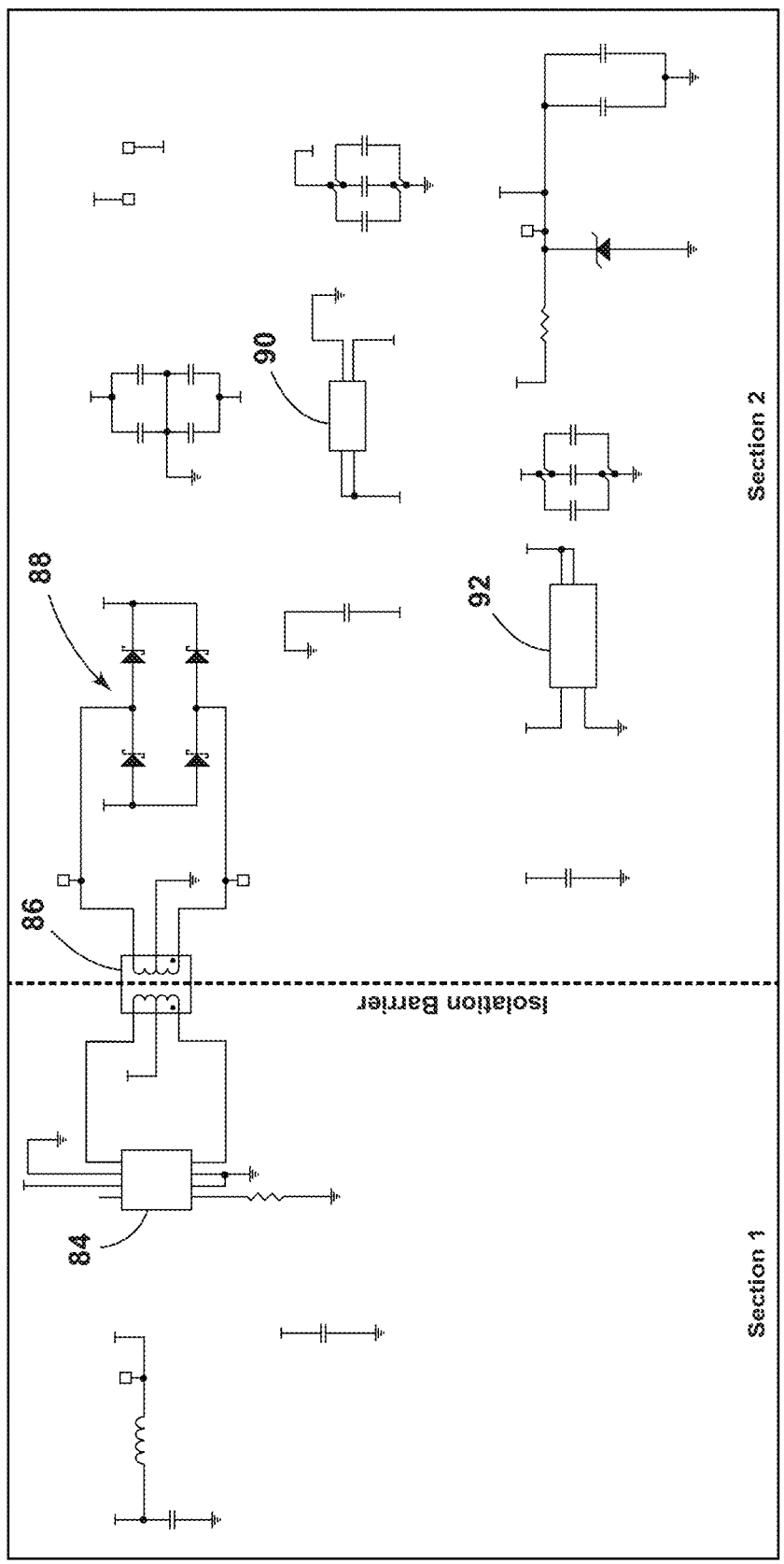
FIG. 12 is a schematic of the power circuit of FIG. 11.

FIG. 12 is a schematic of power circuit_1, which includes various components such as a transformer driver 84 (which may be, for example, part no. MAX845ESA from Maxim), a DC/DC Converter 86 (which may be, for example, part no. TGM-250) along with a diode circuit 88 for generating +2.5 V, a negative low dropout micro power regulator 90 (which may be, for example, part no. LT1175CST from Linear Technology) for generating −5 V, and a low dropout micro power regulator 92 (which may be, for example, part no. LM1117MPX from Texas Instruments) for generating +5 V. Power circuit_1 provides output voltages of +5 V, −5 V and +2.5 V for the input voltage 9 V DC. Section 1 in FIG. 12 shares the ground with Section 1 in FIG. 11. Similarly, Section 2 in FIG. 12 shares the ground with Section 2 in FIG. 11.

Figure 13:
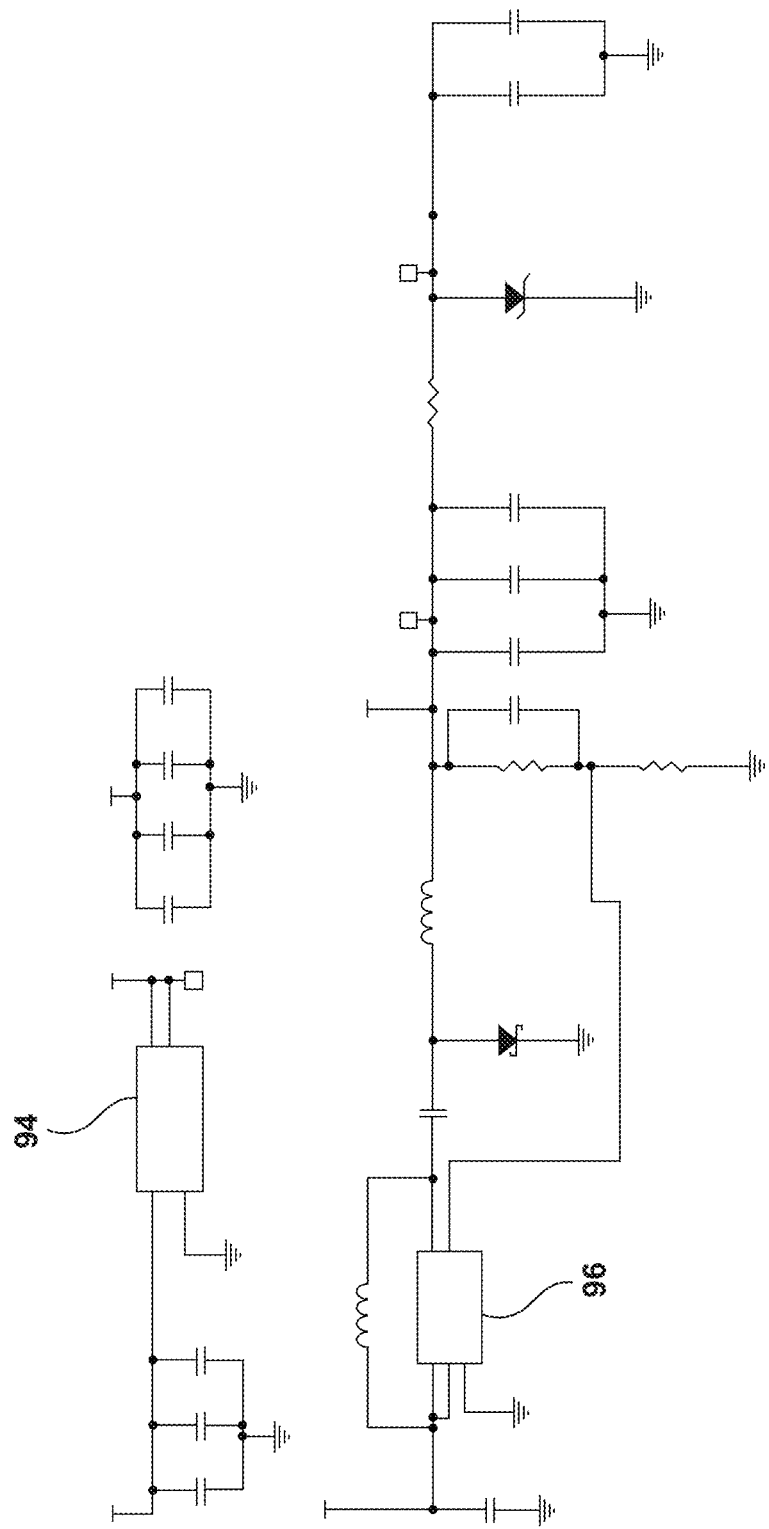
FIG. 13 is a schematic of a second power circuit.

FIG. 13 is a schematic of power circuit_2 which includes various components such as a low-dropout linear regulator 94 (which may be, for example, part no. LM1117MPX from Texas Instruments) for generating +5 V, and a micro power inverting DC/DC converter 96 (which may be, for example, part no. LT1617ES5 from Linear Technology) for generating −5 V and −4.1 V. Power circuit_2 provides output voltages of +5 V, −5 V and −4.1 V for the input voltage 9 V DC. Power Circuit_2 shares the ground with Section 2 of signal conditioning circuit in FIG. 11.

Figure 14A:
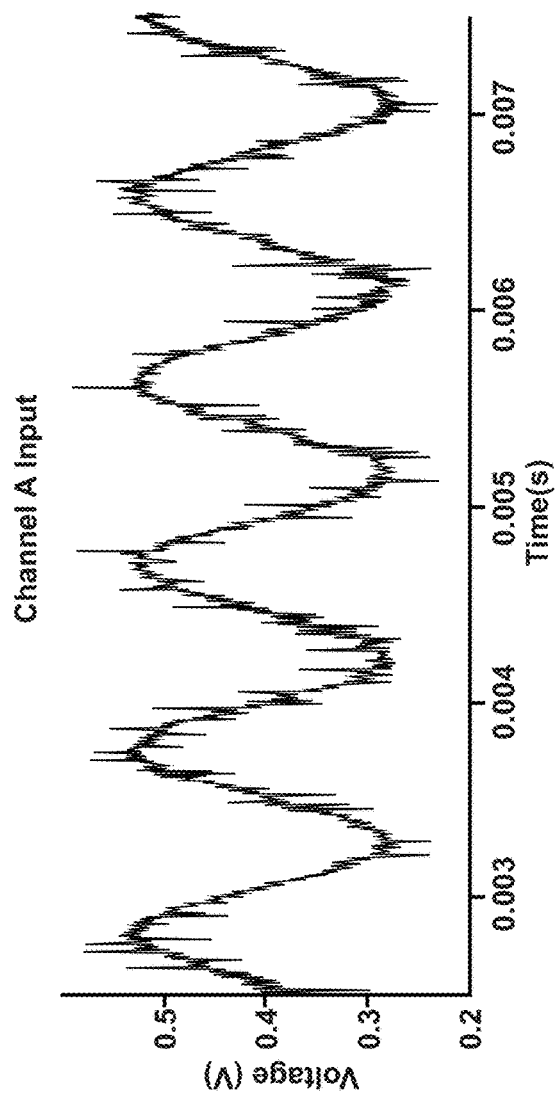
FIG. 14A is a graph showing the result of a single channel input signal of 244 Mv.
Figure 14B:
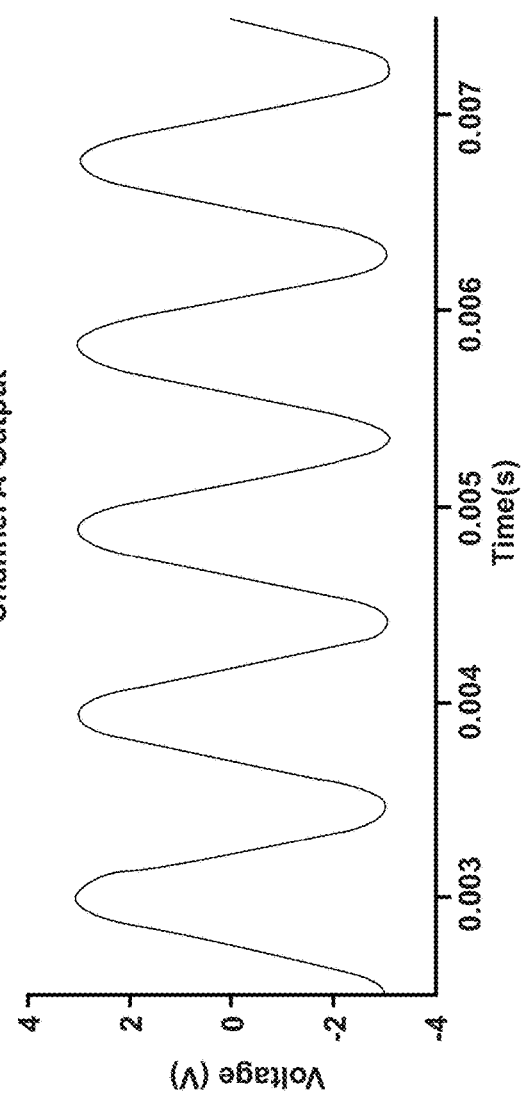
FIG. 14B is a graph showing the amplified output signal (6.08 V) with gain of 24.9 for the single channel input signal of FIG. 14A.
Figure 15:
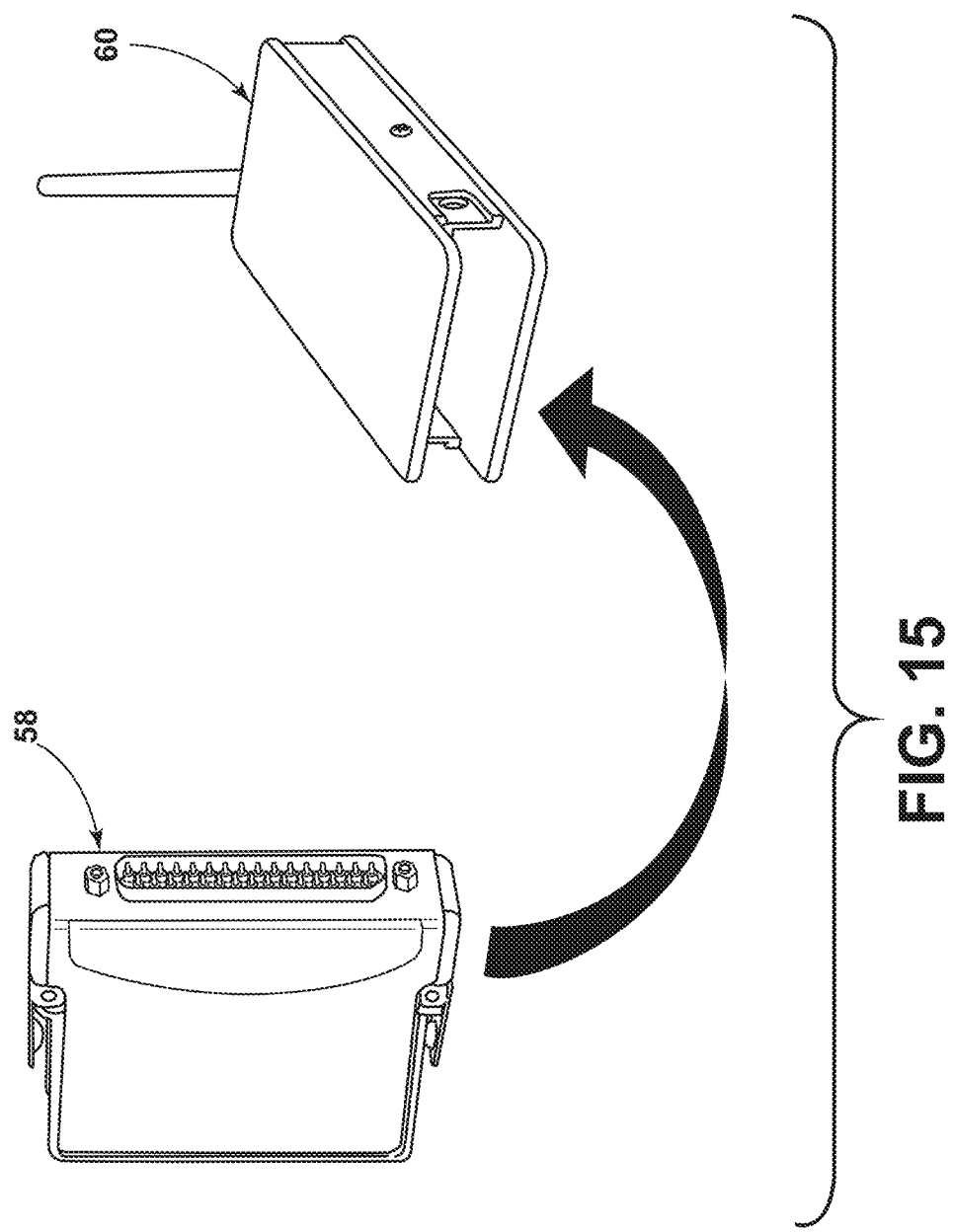
FIG. 15 is an isometric view showing components of a wireless DAQ according to one aspect of the present disclosure.
Figure 16:
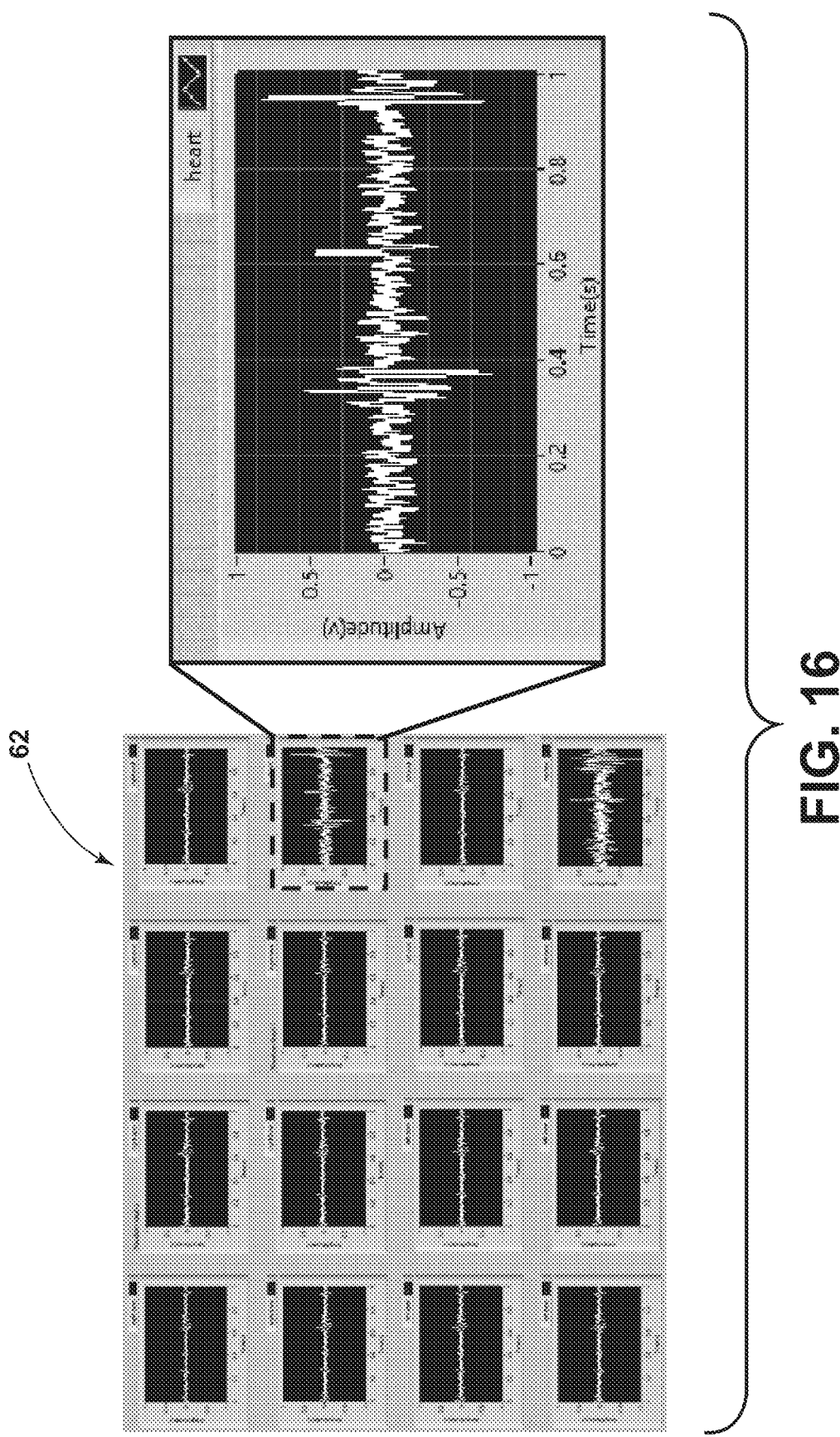
FIG. 16 is a graphical user interface (GUI) showing real time sound waveforms.

After implementing the signal conditioning circuit for single channel on a breadboard (not shown), a STEP file of the 16-channel signal conditioning circuit was generated and a PCB was fabricated. The fabricated 16-channel signal conditioning PCB was mounted with a 44-pin D-sub female connector and a 37-pin D-sub female connector to connect the foam pad 23 and DAQ 28, respectively. The 16-channel signal conditioning circuit may be powered by an AC to DC adapter that converts 100-240V AC to 9 V DC. With reference to FIG. 15, a 244 mV AC ("Channel A Input") is supplied as the input signal at 50 Hz frequency, and an output signal ("Channel A Output") of 6.08 V AC at 50 Hz was observed on a digital oscilloscope with a gain of 24.9 (FIGS. 14A and 14B).

With reference to FIG. 15, a NI-9205 C series voltage input module DAQ system 58 was used to acquire the analog signal from the signal conditioning circuit 52, and the analog signal is converted to a digital signal using an in-built A/D converter. A NI cDAQ-9191 Wi-Fi module 60, with chassis, was used to transmit the digital signals from DAQ 58 to Wi-Fi enabled devices (FIG. 15). These DAQ and Wi-Fi chassis modules were chosen because the DAQ 58 can fit in the Chassis 60 as one unit, providing a compact and portable system.

Bluetooth 4.0 and Wi-Fi 802.11 (a, b, g, n) are known communication protocols for wireless data transmission. Table 1 (below) summarizes the characteristics of Wi-Fi and Bluetooth. Although Bluetooth offers better battery life with lower power consumption when compared to Wi-Fi, the data throughput, bit rate and access range is generally lower for Bluetooth. Wi-Fi wireless transmission was chosen for the systems 1, and 20 because the minimum raw bit rate required is 2.93 Mbps which cannot, at present, be achieved by Bluetooth communication.

| Name | Bluetooth Classic | Bluetooth 4.0 Low Energy (BLE) | ZigBee | WIFI |
| --- | --- | --- | --- | --- |
| IEEE Standard | 802.15.1 | 802.15.1 | 802.15.4 | 802.11 (a, b, g, n) |
| Frequency (GHz) | 2.4 | 2.4 | 0.868, 0.915, 2.4 | 2.4 and 5 |
| Maximum raw bit rate (Mbps) | 1-3 | 1 | 0.250 | 11 (b), 54 (g), 600 (n) |
| Typical data throughput (Mbps) | 0.7-2.1 | 0.27 | 0.2 | 7 (b), 25 (g), 150 (n) |
| Maximum (Outdoor) Range (Meters) | 10 (class 2), 100 (class 1) | 50 | 10-100 | 100-250 |
| Relative Power Consumption | Medium | Very low | Very low | High |
| Example Battery Life | Days | Months to years | Months to years | Hours |
| Network Size | 7 | Undefined | 64,000+ | 255 |

A custom built LabVIEW program 32 (FIG. 4) was developed and implemented in the Wi-Fi enabled device (PC or tablet) to acquire the digital signals from the Wi-Fi module, which were converted and conditioned from lung, heart and trachea sounds sensed by the stethoscopes. In the LabVIEW program, 'DAQ Assistant' function was used to select the data channels (1-16) and the sample rate, which was 8 kHz for one channel and 128 kHz for 16 channels. The 'Waveform Graph' function was used to display the real time waveform signals on the display screen of computer 10, 30. The 'Time Target' function was used to set the sound recording time of the stethograph system for 20 seconds. 'Write to Measurement File' option was used to save the recorded data in a '.lvm' format database. The real time sound waveform sensed by the 16 stethoscopes may be shown simultaneously on the custom built graphical user interface (GUI) 62 (FIG. 16) and the data may be saved in '.lvm' file format.

Figure 17:
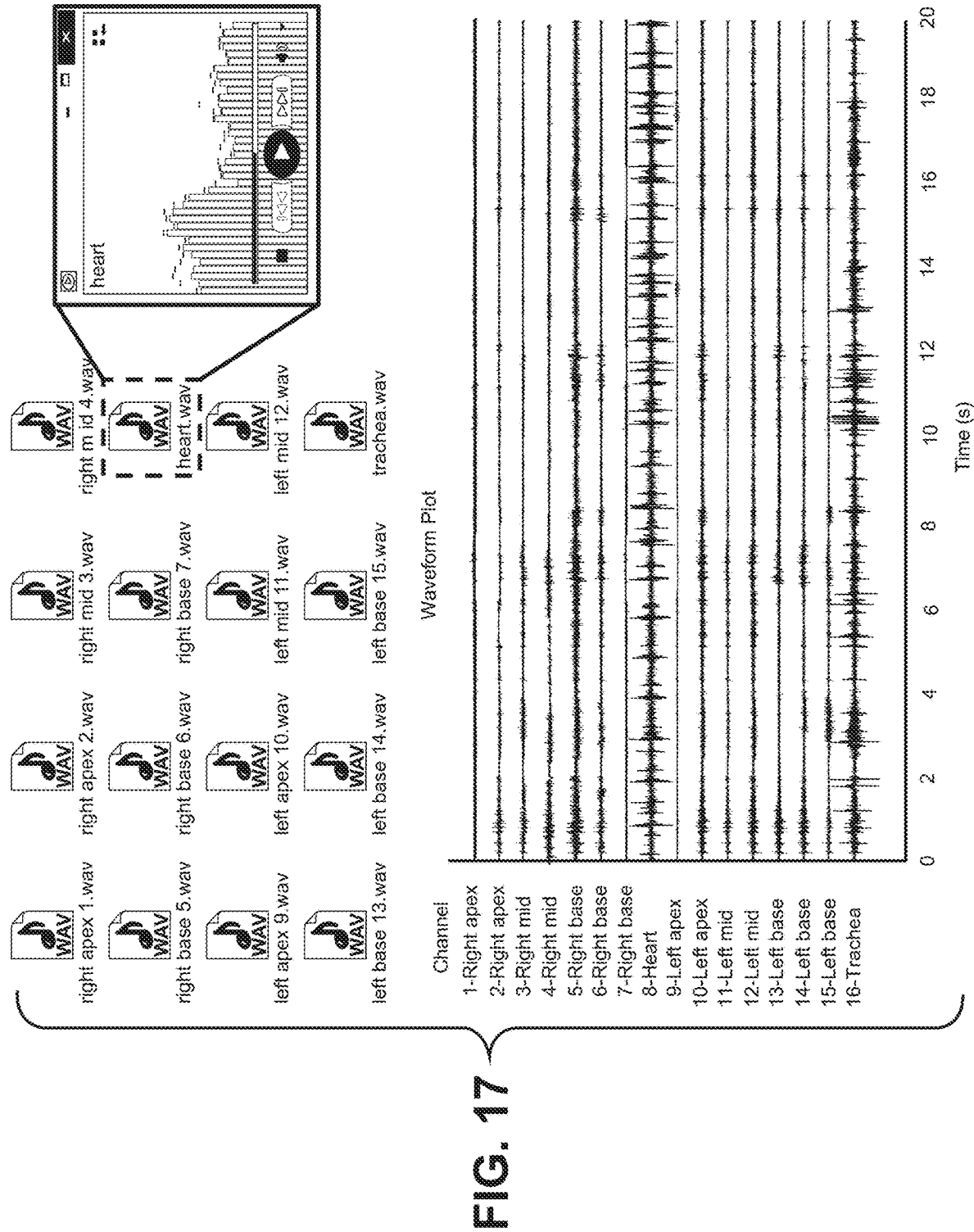
FIG. 17 is a GUI showing audio .WAV files and waveforms that may be utilized to analyze the heart and lung conditions by visual examination.

A MATLAB program 34 (FIG. 4) was developed to convert the recorded data from LabVIEW program into 16 audio files of '.WAV' format (for audio playback) as shown in FIG. 17, and to plot the waveforms for analyzing the heart and the lung conditions by visual examination. The 'textread' command may be used to load the data recorded by LabVIEW and loop logic was used to select the channels. In addition to this, 'audiowrite' command may be used to convert the recorded data to '.WAV' audio format and the 'audioread' command may be used to plot the waveforms from the audio file.

Figure 18:
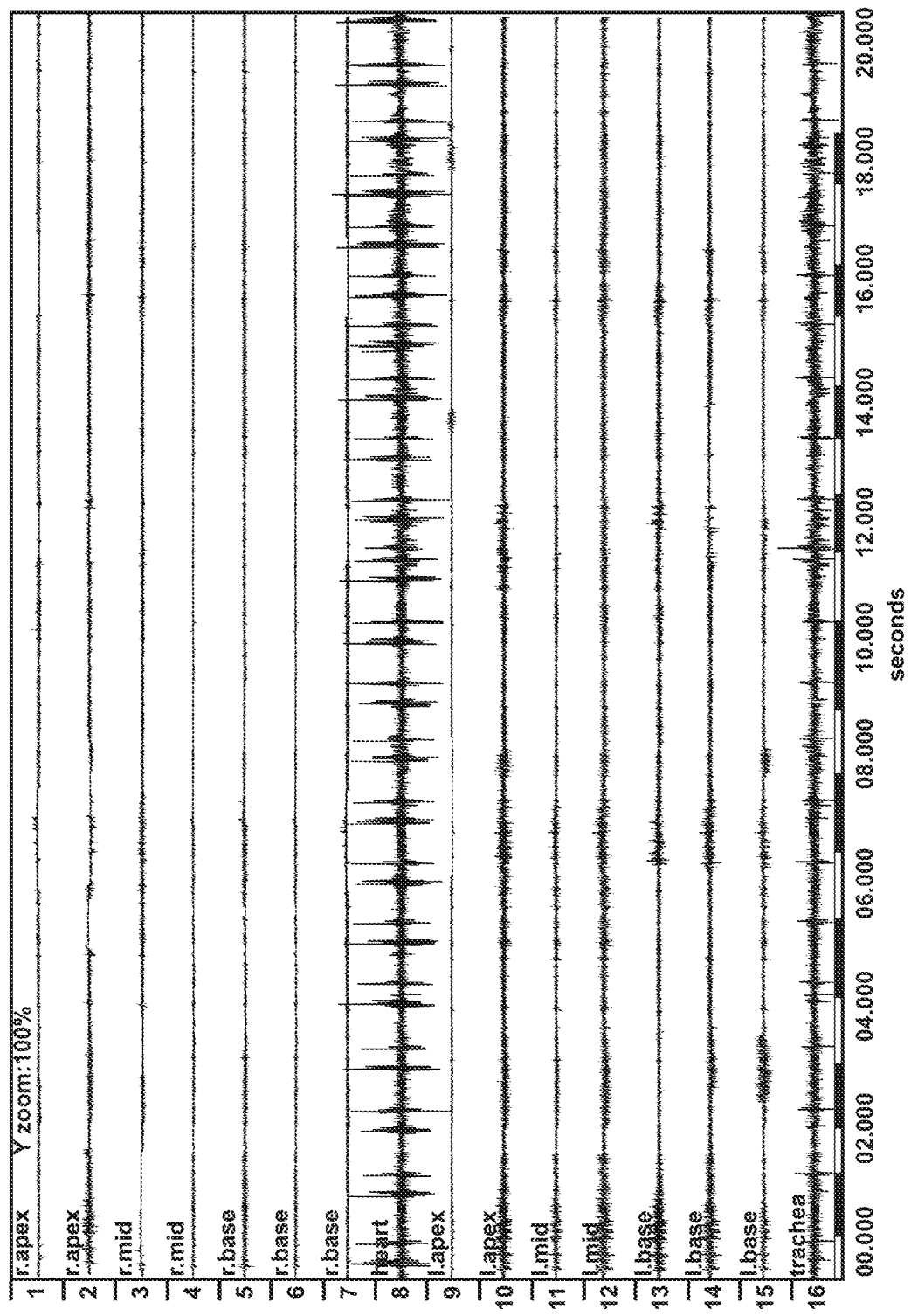
FIG. 18 is a screenshot (GUI) showing waveforms plotted in Version 1.0 by STG 16 software.
Figure 19:
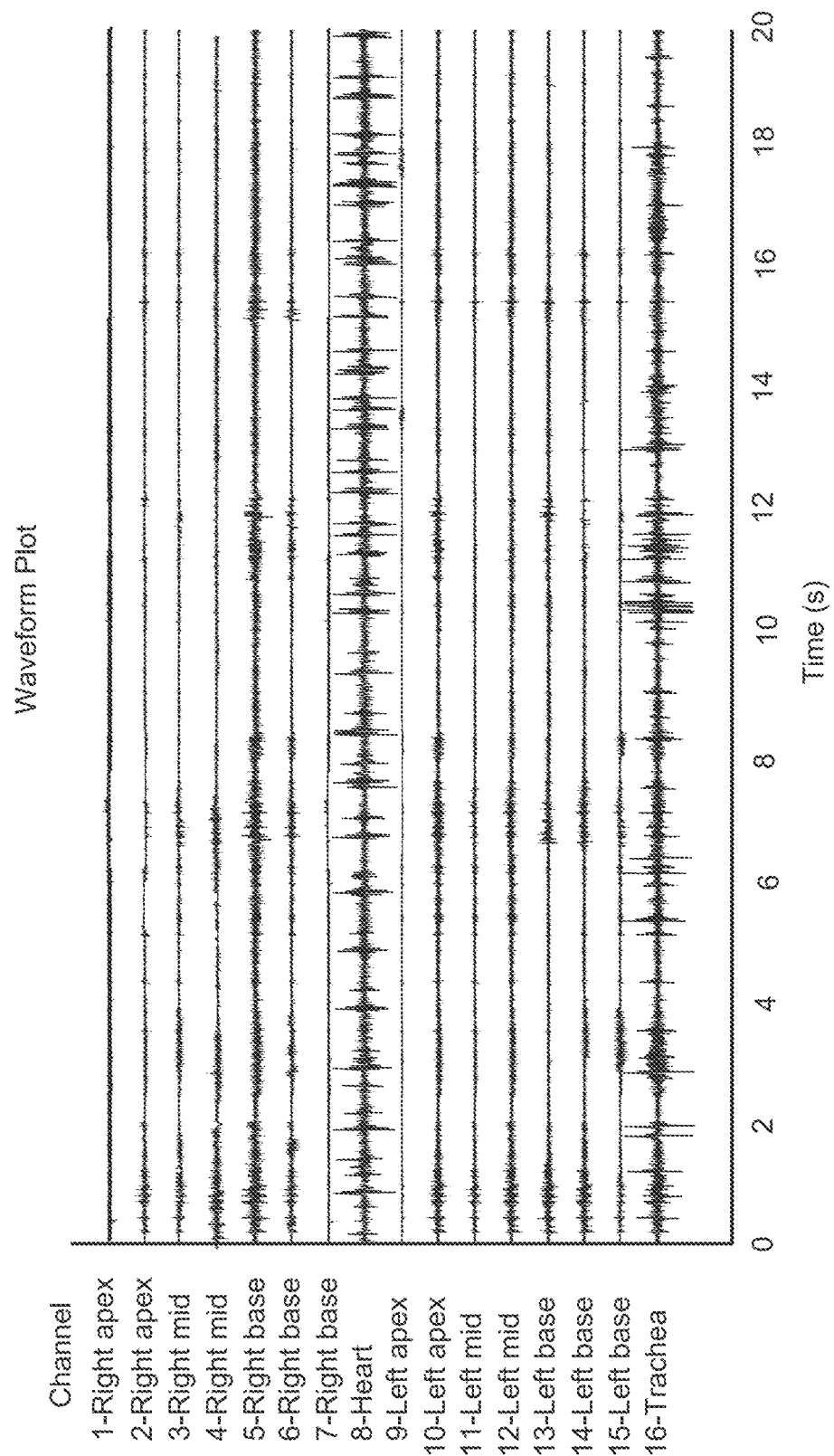
FIG. 19 is a screenshot (GUI) showing waveforms plotted in Version 2.0 by a custom MATLAB program according to one aspect of the present disclosure.

FIGS. 18 and 19 show time unexpanded mode waveforms plotted in stethograph system version 1.0 (by using STG 16 software) and version 2.0 (by using custom built MATLAB program), respectively. The waveforms plotted in the two versions are visually identical. The sounds generated by the heart and trachea are more prominent in amplitudes than the sounds generated by lungs. Thus, the waveforms on channel 8 (heart sound) and channel 16 (tracheal sound) have much higher amplitude than other channels.

To make the version 1.0 software compatible with version 2.0 hardware, the I/O function of the LabVIEW VI program in version 1.0 was replaced with the new I/O function specifying the pin numbers of the channels of the wireless DAQ.

Figure 21:
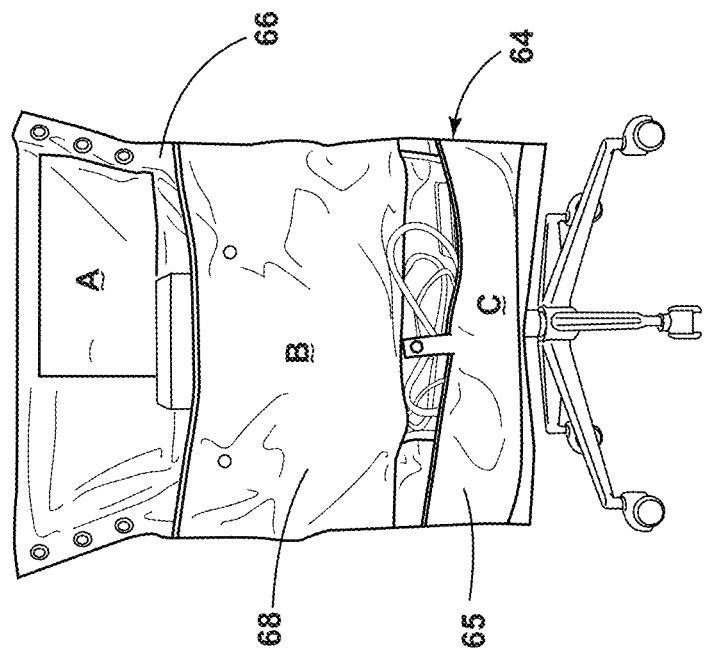
FIG. 21 is a rear perspective view of the chair and organizer of FIG. 20.
Figure 20:
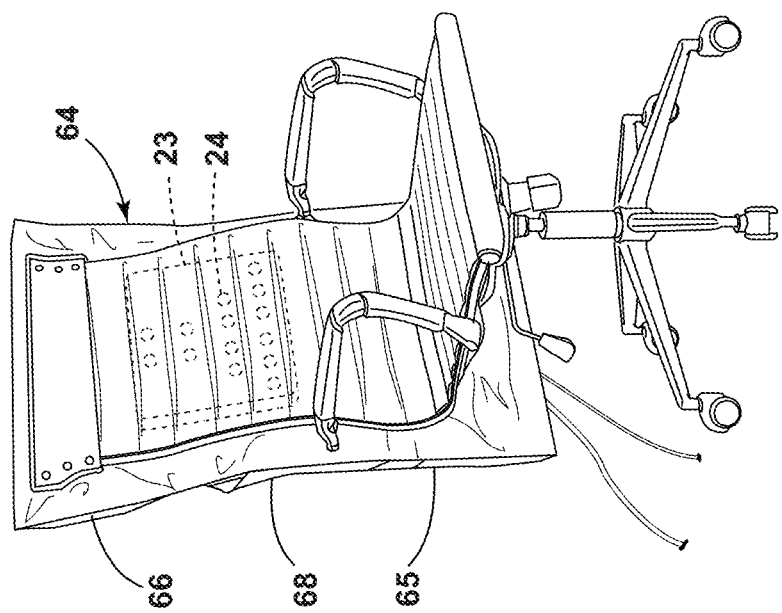
FIG. 20 is a perspective view of a chair and component organizer that may be utilized to support the components of the multi-channel stethograph system in use.

With further reference to FIGS. 20 and 21, a chair 64 having a back 65 may be utilized during patient testing. An organizer 66 made from flexible fabric or other suitable material may be positioned on the chair back 65. The organizer 66 includes pockets A, B, and C as shown in FIG. 21. Pocket A may be utilized to store the stethoscopes, pocket B may be used to store the signal conditioning PCB, and pocket C may be utilized to store the DAQ with Wi-Fi unit. Referring again to FIG. 20, the foam pad 23 with stethoscopes 24 may be positioned on a front side 68 of chair back 65 for patient testing. A patient sitting in chair 64 leans back against the foam pad 23 and stethoscopes 24, thereby permitting the stethoscopes 24 to generate data as discussed above. It will be understood that the additional stethoscopes 25A and 25B may also be connected to the patient's heart (front side of chest) and thorax while the patient is sitting in the chair 64.

Figure 22:
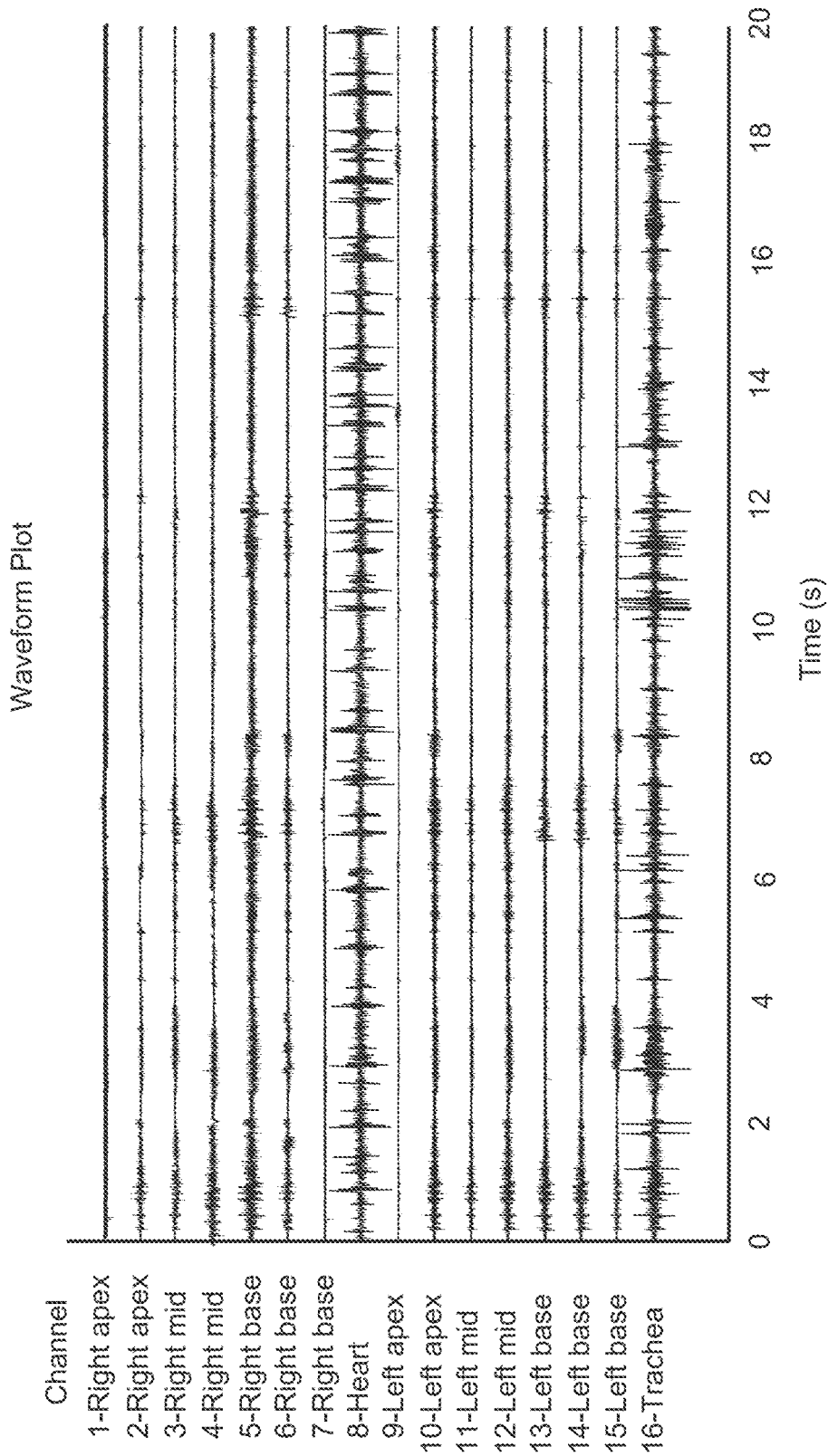
FIG. 22 is a screen shot (GUI) of waveforms generated during testing, wherein the waveforms are generated by a MATLAB program according to one aspect of the present disclosure.
Figure 23:
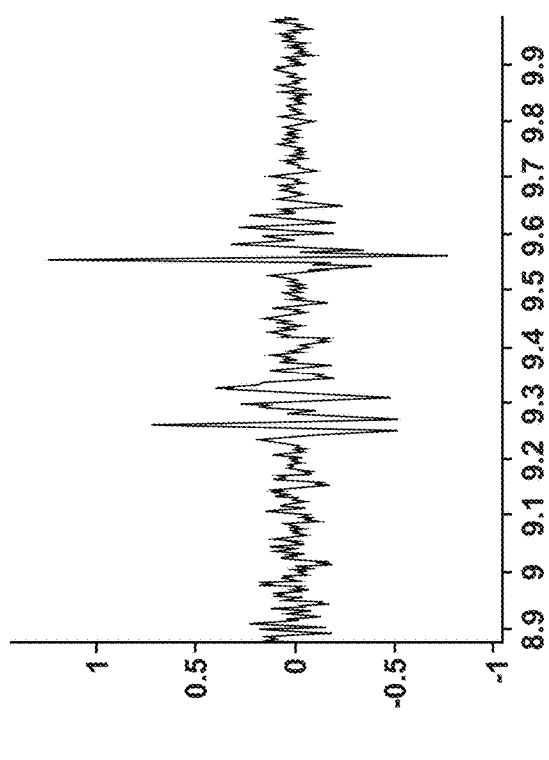
FIG. 23 is a graph (GUI) showing the time expanded waveform of a heart sound generated during testing of a device according to one aspect of the present disclosure.
Figure 24:
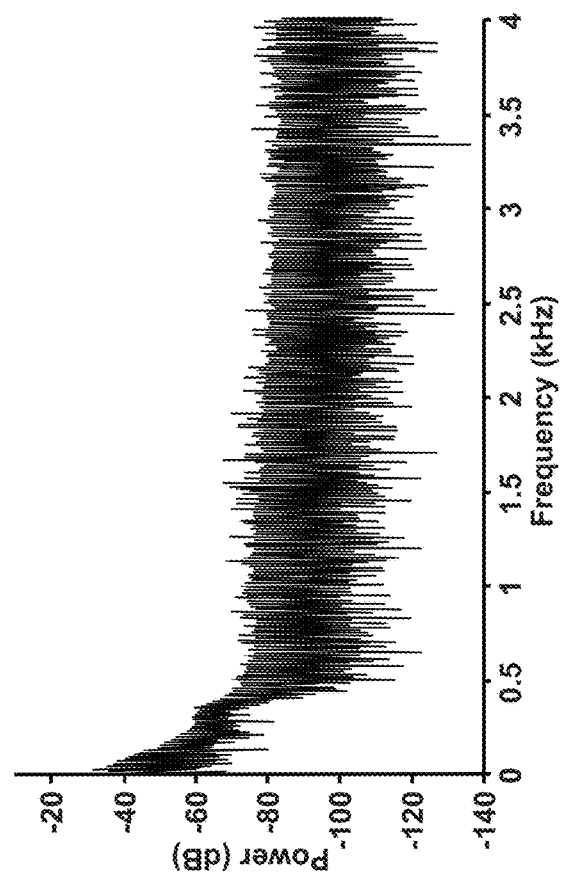
FIG. 24 is a graph (GUI) showing the signal-to-noise ratio of a heart signal measured by a MATLAB program according to one aspect of the present disclosure.

With further reference to FIGS. 22-24, testing of a multichannel stethograph system 20 according to the present disclosure resulted in the waveforms shown in FIG. 22. More specifically, FIG. 22 is a screen shot (GUI) of a screen shot computer 30 showing the output of a MATLAB program according to one aspect of the present disclosure. FIG. 23 is a screen shot (GUI) showing a time expanded waveform of a heart sound generated during testing of a multichannel stethograph system according to the present disclosure. FIG. 24 is a graph (GUI) showing the signal-to-noise ratio of a heart signal measured by a MATLAB program according to one aspect of the present disclosure.

The waveforms in time domain were analyzed and converted to spectrograms as well as frequency domain using digital signal processing techniques such as continuous wavelet transform (CWT) and fast Fourier transform (FFT)/discrete Fourier transform (DFT) by MATLAB® Script, respectively. The time domain plots, frequency domain plots, and spectrograms provide information about the inspiration, expiration and heart rhythms from the recorded lung, heart and trachea sounds. Any abnormal patterns such as crackles, squawks, wheeze, rhonchi, and rale can be identified and analyzed from the plotted waveforms in time domain, frequency domain and spectrogram with the help of custom designed algorithms developed using box filter, signal envelope, digital filter, 2-D correlation coefficient and cross-correlation. These custom developed algorithms are employed to identify and diagnose the disease conditions such as Pneumonia, Chronic obstructive pulmonary disease (COPD), Asthma, Congestive heart failure (CHF), Vocal cord dysfunction (VCD).

Methods such as statistical analysis, digital signal processing (CWT, FFT, DFT, short-time Fourier transform (STFT)) or artificial intelligence (AI) methods such as neural networks (shallow neural networks, deep convolution neural networks), support vector machine (SVM), and K-nearest neighbor (KNN) may be used for classification and identification. The methods can be developed on platforms such as MATLAB® Script, C, C++, Python, C#, Perl programming languages.

The components such as signal conditioning circuit and wireless DAQ module can be fabricated into a single compact and miniaturized PCB module, and placed within the foam pad as shown in FIG. 1.

Figure 25:
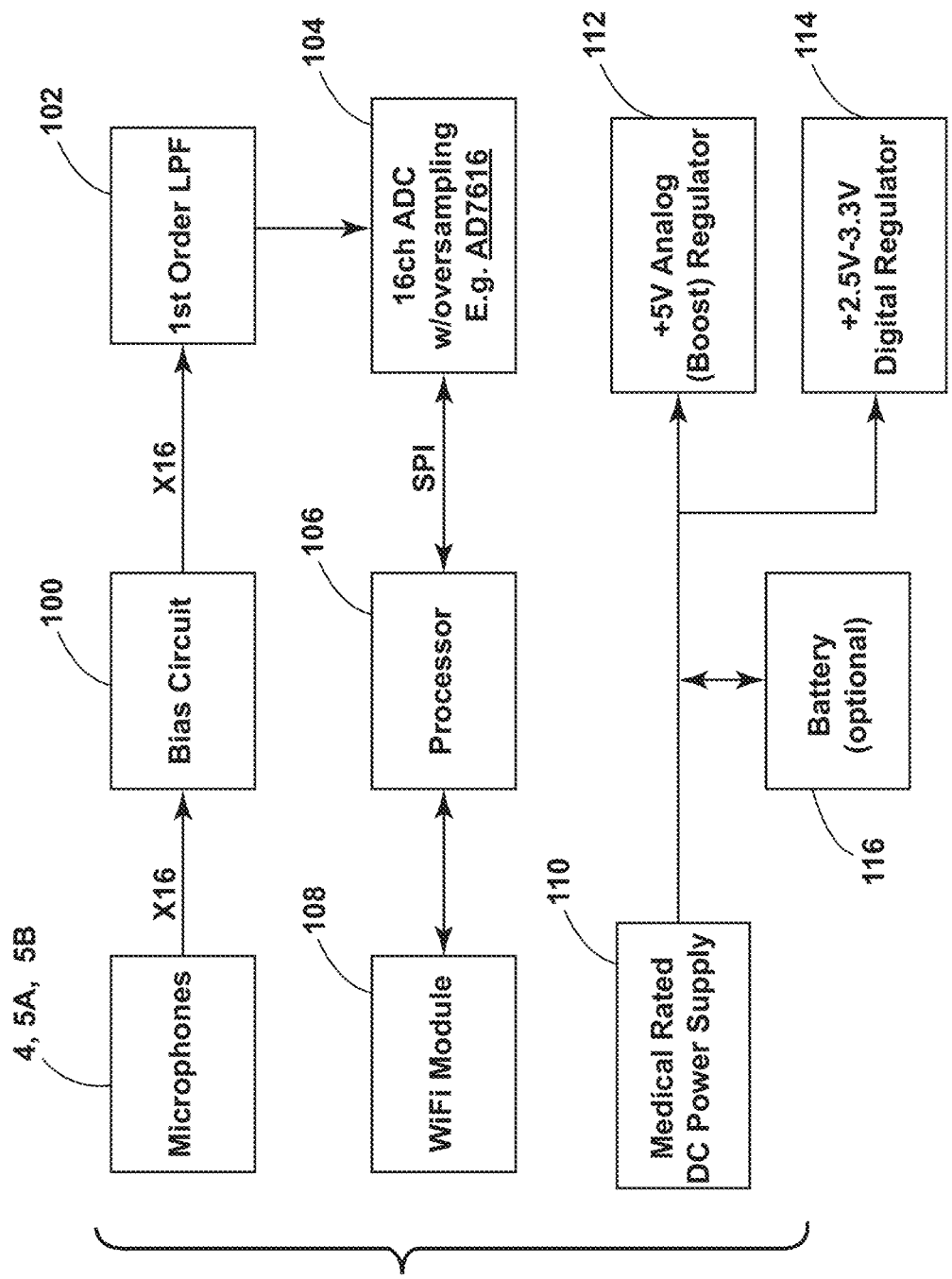
FIG. 25 is an electrical circuit diagram in block form of a wireless stethograph system according to one aspect of the present disclosure.

As shown in FIG. 25, miniaturization may be implemented using a bias circuit 100, a first order low pass filter 102, a 16-channel ADC integrated circuit 104 paired with a microprocessor 106 with Wi-Fi capabilities or interfaced with an off-the-shelf Wi-Fi module 108. Isolation may be accomplished with a medical-rated DC power supply 110 providing power to a +5V analog boost regulator 112 and a +2.5V-3.3V digital regulator 114 with an optional battery 116. A quality ADC with low voltage range, built-in buffers, and digital oversampling can greatly simplify the design so that even active components might be eliminated from the design.

Figure 27:
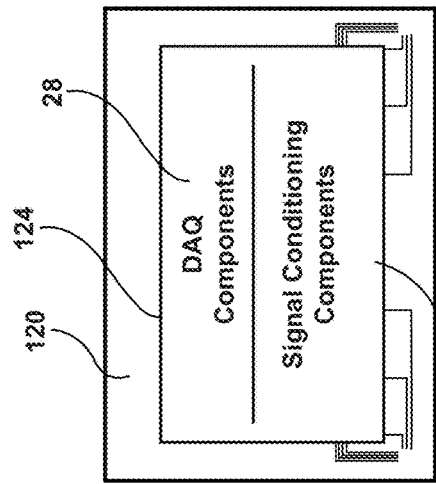
FIG. 27 is a back view of the stethograph system of FIG. 26.
Figure 26:
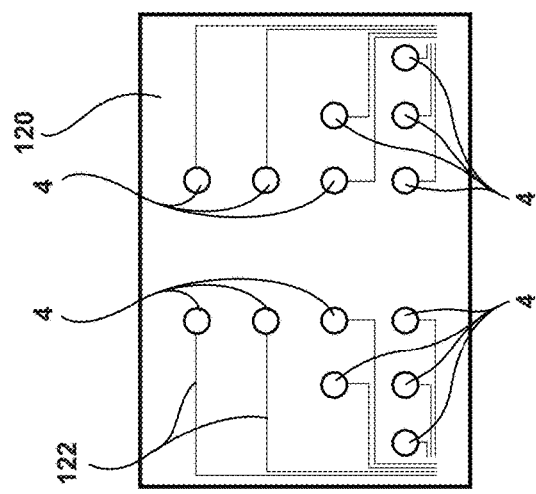
FIG. 26 is a front and back view of a wearable version of a wireless stethograph system according to one aspect of the present disclosure.

A multichannel stethograph system according to the present disclosure may be implemented as a wearable device that may be attached either directly to the skin or integrated in to a jacket/cloth for continuous monitoring of lung and heart conditions. As shown in FIGS. 26 and 27, this may be achieved by developing the system on a flexible substrate 120. Substrate 120 may comprise a suitable polyester film such as polyethylene terephthalate (PET), polyethylenenaphthalate (PEN); polyimide films such as Kapton, Upilex; paper/coated papers; polyurethane plastics/thermoplastic elastomers such as thermoplastic polyurethane; silicon based organic polymers such as polydimethylsiloxane (PDMS), or Ecoflex. The array of microphones 4 and electrical components 124, including signal conditioning components 26 and DAQ components 28, may be surface mounted on flexible substrate 120. The interconnects for the circuit can be deposited using additive print manufacturing processes such as screen, inkjet, flexography, aerosol jet or gravure. The materials used for printing may include non-transparent, transparent, flexible and stretchable inks that could be conductors, semi-conductors and dielectrics.

Figure 28:
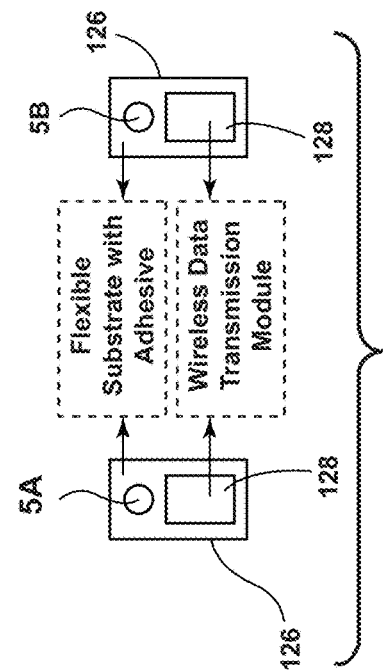
FIG. 28 is a schematic view of flexible microphone patches of the system of FIGS. 26 and 27 for the heart and trachea.

With reference to FIG. 28, surface mounted microphones 5A and 5B may be attached to flexible substrate patches 126. Circuits 128 may have wireless capabilities, and may be placed close to the heart and trachea of a patient using adhesives to thereby acquire heart and trachea sounds. The system may be powered using either conventional batteries or printed and flexible batteries. The data collected from the flexible and hybrid multichannel stethograph system may be wirelessly streamed and stored in cloud networks or health care servers for maintaining and accessing patient records remotely.

A multi-channel stethograph system according to the present disclosure may be configured to record and plot heart and lung sounds non-invasively using 16 stethoscopes. It will be understood, however, that the present disclosure is not limited to exactly 16 stethoscopes, and more or fewer stethoscopes may be utilized as required for a particular application. As discussed above, the stethoscopes may be fabricated by placing microphones in a CNC machined polymer material covered material that is covered using a diaphragm. Fourteen of the stethoscopes may be positioned in a memory foam pad 23, and two may be placed directly on the heart and trachea. This enables the system to acquire sound simultaneously from the lung, heart, and trachea. The sounds acquired from the 16 stethoscopes are processed through a custom designed 16-channel signal conditioning printed circuit board (PCB). A data acquisition system (DAQ) and Wi-Fi chassis may be used to acquire and wirelessly transmit the data from the 16-channel PCB to a Wi-Fi-enabled computing device such as a personal computer (PC) or tablet computing device. The system preferably includes a custom LabVIEW program developed on the Wi-Fi enabled device to record the data from the DAQ. In addition, a MATLAB program was developed to convert the recorded data from the stethoscopes into 16 audio files for audio playback, and to plot the waveforms in time domain.

The system preferably has an amplification gain of at least about 24, and a signal to noise ratio of at least about 15.27 dB (measured for the heart signal). The recorded audio files and plotted waveforms of the lung, heart and trachea sounds demonstrated that the multi-channel stethograph system 20 may be utilized for visual examination to determine if abnormal patterns in inspiration and expiration are present. The stethographic device/system provides information to a physician to facilitate diagnosing and analyzing the condition of a patient's heart and lungs.

Figure 29:
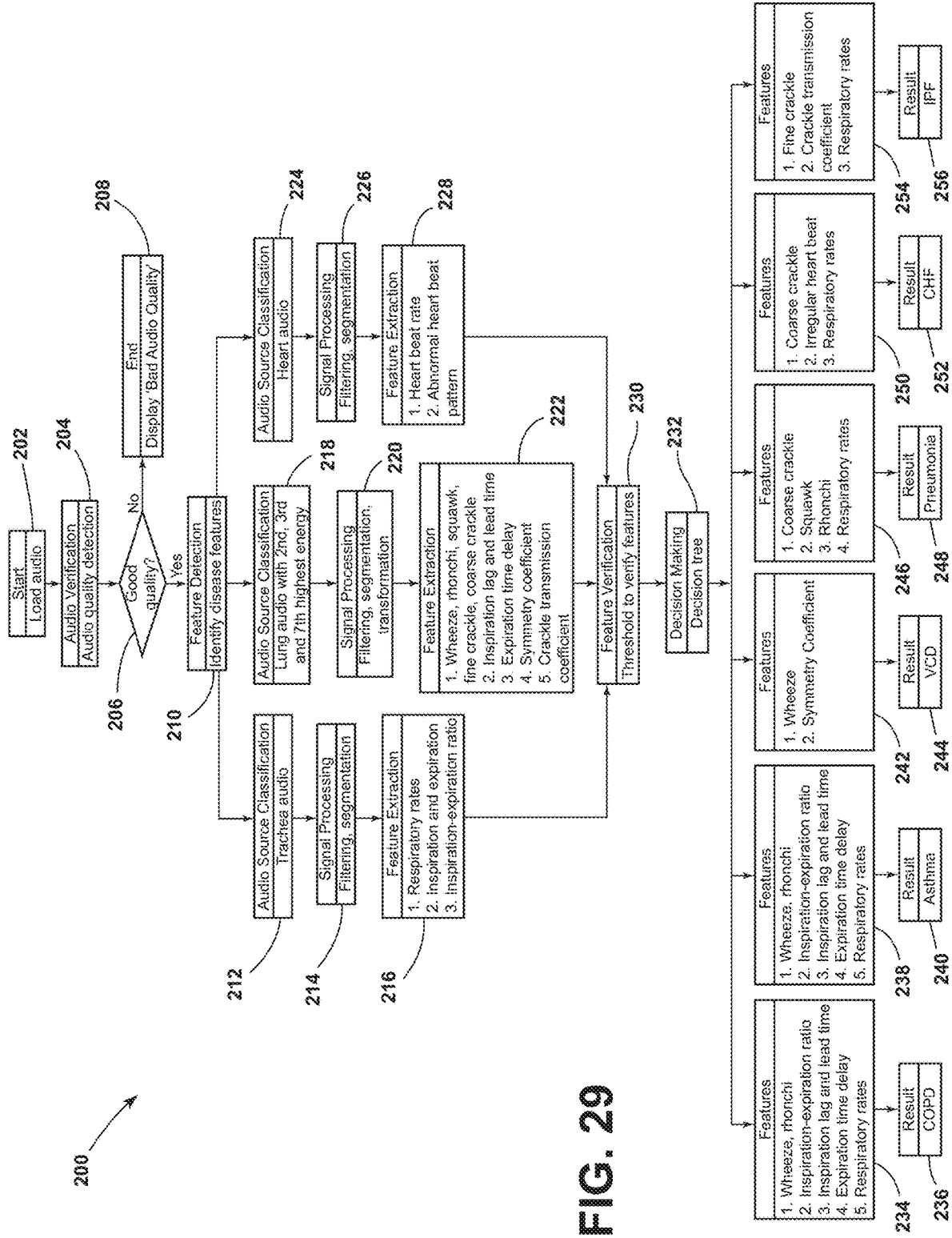
FIG. 29 is a flowchart of an Auscultation Diagnosis Program (ADP) or method for disease detection according to another aspect of the present disclosure.

With further reference to FIG. 29, a diagnostic process according to another aspect of the present disclosure may comprise a MATLAB-based Auscultation Diagnosis Program (ADP) 200. ADP 200 may be utilized by computer (FIG. 1) or other suitable device to analyze audio from the heart, lungs and trachea (HLT) using various digital signal processing techniques. The HLT sound analysis method may allow for more precise auscultation when compared to diagnosing a patient using the conventional stethoscope based method. The HLT audio may be non-invasively measured using the multi-channel stethograph system 1, described above in connection with FIGS. 1-28. System 1 may be configured to record audio through a set of 16 microphone sensors, including fourteen stethoscopes 4, and stethoscopes 5A and 5B for heart and thorax (e.g. FIG. 2). The ADP 200 may be configured to filter and distinguish between good (acceptable) and bad (unacceptable) quality audio utilizing predefined acceptance criteria. ADP 200 may also be configured to identify abnormal features or parameters in the HLT sound. ADP 200 may comprise a decision tree algorithm that utilizes abnormal features and/or parameters to distinguish among diseases. The diseases may include chronic obstructive pulmonary disease (COPD) 236, asthma 240, vocal cord dysfunction (VCD) 244, pneumonia 248, congestive heart failure (CHF) 252, and interstitial pulmonary fibrosis (IPF) 256.

ADP 200 uses digital signal processing techniques to examine the quality of the HLT audio. At step 202, the process (program) starts by loading the HLT audio data set, collected by the multi-channel stethograph device 1, into the program. This data set may include 16 audio files (1 for heart audio, 1 for trachea audio and 14 for lung audio). The ADP 200 may include three main phases: (a) audio verification (steps 202-208), (b) feature detection (steps 210-230) and (c) decision making (steps 232-256).

During the audio verification phase, the ADP 200 examines the quality of the HLT audio (step 204). At step 206 of the audio verification phase, the system (utilizing ADP 200) determines if the quality of the audio meets predefined criteria and, if not, alerts the user of a low quality audio (step 208). This reduces or prevents the detection and identification errors that could be caused by low quality audio recordings. Four conditions that may cause a bad quality audio include (1) audio including shallow breath, (2) audio including loud environment noise, (3) audio including man-made noise and (4) audio of insufficient length (e.g. less than about 20 seconds). The ADP 200 may be configured to cause computer 10 (FIG. 1) or other device to display a message 'Bad Audio Quality' (step 208) if the audio data sets includes 'bad quality' HLT sounds otherwise it will proceed to the next phase.

During the feature detection phase, any abnormal features of the HLT audio are detected/identified and extracted for identification of the diseases. This phase includes three steps: (1) audio source classification (steps 212, 218, and 224); (2) signal processing (steps 214, 220, and 226); and (3) feature extraction (steps 216, 222, and 228).

During audio source classification, the audio data set is classified based on its source: i.e. trachea (step 212), lung (step 218), or heart (step 224). This is done to efficiently and accurately identify and extract features that are specific to each source. For optimization, from among 14 audio files for the lungs, the audio with $2^{nd}$, $3^{rd}$ and $7^{th}$ highest energies may be calculated and selected for further processing.

During signal processing, the audio signals are processed by filtering and segmentation (steps 214, 220, and 226). Filtering may be utilized to eliminate white noise, and to select only the signals within frequency ranges corresponding to each source (e.g. eliminate signals having frequencies that are clearly outside of a range of expected or possible values). Segmentation is then done for enveloping the signal in time and frequency waveform to provide a clear trace of the signal. For the lung audio, transformation is performed to transform the processed signal to a time-frequency waveform.

During feature extraction (steps 216, 222, and 228), the features corresponding to each source are extracted from the processed signals. From the trachea audio (step 216), parameters including respiratory rates, inspiration and expiration, inspiration-expiration ratio are extracted using time expanded waveform analysis. This analysis may include techniques such as filtering, hamming window, envelop detection, decimation, peak detection and thresholds. With regards to the lung audio (step 222), adventitious sounds including one or more of wheeze, rhonchi, squawk, coarse crackle and fine crackle are extracted, with their corresponding frequency. In addition, other parameters such as inspiration lag and lead time, expiration time delay, crackle transmission coefficient and symmetry coefficient may also be calculated. The feature extraction may be based on time expanded waveform analysis, frequency waveform analysis and time-frequency waveform analysis. The techniques may include one or more of filtering, hamming window, fast Fourier transformation, decimation, interpolation, peak detection, zero crossing, thresholds, cross-correlation and nearest neighbor. From the heart audio (step 228), the heartbeat rate and any abnormal heartbeat patterns are extracted. This extraction may comprise time expanded waveform analysis. The techniques utilized in this analysis may include filtering, hamming window, envelop, decimation, peak detection and thresholds. The filtering process may use a bandpass filter with frequency between about 50 Hz and about 600 Hz to eliminate unwanted signals including environmental and human body noise. It will be understood that other lower frequency boards may be utilized (e.g. 20 Hz, 30 Hz, 40 Hz, 60 Hz, 70 Hz, 80 Hz, etc.). Similarly, the upper frequency boards may be utilized, in any combination, with different lower frequency boards. For example, upper frequency boards of 400 Hz, 500 Hz, 700 Hz, 800 Hz, 900 Hz, 1,000 Hz, etc. may be utilized. The Fast Fourier Transformation method computes and converts the audio signal from the time waveform to the frequency waveform. The Hamming window and envelop detection process is used to estimate the instantaneous magnitude of the audio signal in both time and frequency domain of the waveforms. The decimation process is associated with downsampling the audio signal by a ratio of 100 in both the time and frequency waveform for reducing data size. Interpolation is the process of upsampling the audio signal by a ratio of, for example, 100 in both the time and frequency waveform to increase the data size back to its original sample rate. Peak detection and thresholds may be used for detecting abnormal parameters from the audio signal. The nearest neighbor process may be used for finding the same breath cycle in the trachea and lung sounds. Zero crossing may be used to determine the point where the mathematical sign of the audio signal changes between positive and negative and is used to calculate the average frequency of a certain period. Cross-correlation is the method to measure the similarity of the wheeze that is recorded by the microphones from the left and right lungs.

After the feature extraction process of steps 216, 222, and 228 are completed, the extracted features are then verified (step 230) based on a set of pre-determined thresholds and patterns.

COPD is a chronic inflammatory lung disease that causes obstructed airflow from the lungs. Audio-based diagnosis of COPD may be based on identifying wheeze, rhonchi, inspiration-expiration ratio (< about 0.7), inspiration lag and lead time (> about 3 ms), expiration time delay (> about 3 ms) and respiratory rates (< about 12 or > about 25 breaths per minute). It will be understood that the present disclosure is not limited to the numerical values noted above for inspiration-expiration ratio, inspiration lag and lead time, expiration time delay, and respiratory rates, and other values or criteria may be utilized.

Wheeze and rhonchi are continuous adventitious lung sounds with high and low frequency, respectively. Inspiration-expiration ratio shows the difference between time duration of inspiration and expiration. For example, a patient with COPD may lack supportive tissue and may have a longer exhale time, thus resulting in a low inspiration-expiration ratio. Inspiration lag and lead are time-based parameters in patients with COPD. This is caused due to a mismatch in the start and end time of the inspiration at the trachea and lung. Expiration time delay may be utilized to determine the time delay between expirations. Patients with COPD tend to have prolonged expirations when compared to normal subjects. Respiratory rates may be utilized to determine if a patient is experiencing shortness of breath, which is another symptom of COPD.

Asthma is a chronic lung disease that inflames and narrows the airways. Audio symptoms of asthma that may be present in the audio data may include wheeze, rhonchi, inspiration-expiration ratio (< about 0.7), expiration time delay (> about 3 ms) and respiration (respiratory) rates (< about 12 or > about 25 breaths per minute). COPD and asthma typically have similar symptoms. It will be understood, however, that the present disclosure is not limited to these numerical values, and other values or criteria may be utilized. A distinguishing characteristic between the two diseases is inspiration lag and lead time. When compared to patients with COPD, inspiration lag and lead time are typically not present in patients with asthma.

VCD is an upper airway obstruction caused by abnormal adduction of the vocal cords. Audio symptoms of VCD may include wheeze and symmetrical wheeze at both lungs. In this disease, the wheeze is generated closer to the vocal cord than the lung. Therefore, the wheeze is more symmetrically distributed over the chest than peripherally distributed wheezes such as those of asthma or COPD patients. A cross-correlation algorithm may be applied to calculate the symmetry coefficient. If the symmetry coefficient is at or above a predefined level (e.g. about 0.5, or other suitable criteria), the ADP may determine that VCD is a likely diagnosis.

Pneumonia is a lower respiratory lung infection that affects primarily the small air sacs. Audio symptoms may include features include coarse crackles, rhonchi, squawk and respiratory rates (< about 12 or > about 25 breaths per minute). Coarse crackles are discontinuous adventitious lung sounds with low frequency (< about 333 Hz). Squawks are short durations of wheeze (< about 100 ms), but it cannot be characterized as a crackle because of the quick sinusoidal waveform.

CHF is a chronic progressive condition that affects the pumping power of the heart muscles and function of the lungs. Audio features of CHF may include coarse crackle (< about 333 Hz), irregular heartbeat and respiration rates (< about 12 or > about 25 breaths per minute). The irregular heartbeat includes a heartbeat rates (> about 100 beats per minute) and a non-uniform heartbeat pattern. It will be understood, however, that the present disclosure is not limited to these numerical values, and other values or criteria may be utilized.

IPF is a chronic lung disease that causes progressive scarring of the lungs. Audio features of IPF may include fine crackles (> about 333 Hz), crackle transmission coefficient (< about 0.5) and respiration rates (< about 12 or > about 25 breaths per minute). It will be understood, however, that the present disclosure is not limited to these numerical values, and other values or criteria may be utilized. A discontinuous adventitious lung sound with high frequency, at the bases of the lungs is a common adventitious lung sound for IPF. Also, the transmission of crackles occurs in a smaller area when compared with patients who have pneumonia and CHF.

It is to be understood that variations and modifications can be made on the aforementioned structure without departing from the concepts of the present disclosure, and further it is to be understood that such concepts are intended to be covered by the following claims unless these claims by their language expressly state otherwise.

The disclosure claimed is:

1. A multichannel wireless stethograph system comprising:
  a plurality of electronic stethoscopes each having a signal in a separate channel corresponding to sounds detected thereby;
  a signal condition circuit for receiving the signals from the plurality of electronic stethoscopes and for filtering and amplifying the signals;
  a data acquisition circuit for receiving filtered and amplified signals from the signal condition circuit and for digitizing the filtered and amplified signals;
  a wireless transmitter for receiving digital signals from the data acquisition circuit and for wirelessly transmitting digital signals;
  a wireless receiver for receiving transmitted digital signals from the wireless transmitter and for outputting the digital signals;
  a processor for processing and analyzing the digital signals received from the wireless transmitter; and
  a display for displaying processed signals received from the processor,
  wherein the signal condition circuit comprises:
    a second order high pass filter stage for filtering the signals from the plurality of electronic stethoscopes;

an isolator amplifier stage for isolating DC voltage and amplifying and transmitting AC voltage of filtered signals received from the second order law-high pass filter stage;

a second order active low pass filter stage for filtering signals received from the isolator amplifier stage;

a third order active high pass filter stage for filtering signals received from the second order active low pass filter stage;

a non-inverting amplifier stage for amplifying the signals received from the third order active high pass filter stage; and a first order passive low pass filter stage for filtering signals received from the non-inverting amplifier stage.

2. The multichannel wireless stethograph system of claim 1, including:

a foam pad for securing at least a subset of the plurality of electronic stethoscopes in a predefined pattern such that when the foam pad may be placed on a patient's torso, wherein each of the subset of the plurality of electronic stethoscopes is simultaneously positioned against the patient.

3. A signal conditioning circuit for a multichannel stethographic system, the signal conditioning circuit comprising:

a second order high pass filter stage for filtering the signals from the plurality of electronic stethoscopes;

an isolator amplifier stage for isolating DC voltage and amplifying and transmitting AC voltage of filtered signals received from the second order high pass filter stage;

a second order active low pass filter stage for filtering signals received from the isolator amplifier stage;

a third order active high pass filter stage for filtering signals received from the second order active low pass filter stage;

a non-inverting amplifier stage for amplifying the signals received from the third order active high pass filter stage; and a first order passive low pass filter stage for filtering signals received from the non-inverting amplifier stage.

4. The signal conditioning circuit of claim 3, wherein:
the stages together provide a signal-to-noise ratio of at least about 15.27 dB.

5. The signal conditioning circuit of claim 3, wherein:
the stages together function as a band pass filter having a frequency range of about 50 Hz to about 1600 Hz.

6. The signal conditioning circuit of claim 3, wherein:
the stages together provide a gain of at least about 24.

7. The signal conditioning circuit of claim 3, wherein:
the second order high pass filter stage has a cut-off frequency of about 2.3 Hz;
the second order active low pass filter stage has a cut-off frequency of about 1600 Hz;
the third order active high pass filter stage has a cut-off frequency of about 50 Hz; and
the first order passive low pass filter stage has a cut-off frequency of about 1600 Hz.

8. A method of diagnosing heart and lung diseases of a patient, the method comprising:

utilizing a plurality of stethoscopes to generate a plurality of audio data sets corresponding to each stethoscope, wherein the audio data sets comprise:

a) at least one data set generated by a heart stethoscope positioned on the patient to generate a heart audio data set;

b) at least one trachea data set generated by a trachea stethoscope positioned on the patient to generate a trachea audio data set; and c) a plurality of lung data sets generated by a plurality of lung stethoscopes positioned on the patient;

utilizing a signal conditioning circuit for receiving signals from the plurality of stethoscopes and for filtering and amplifying the signals to provide the audio data sets;

utilizing a computing device to extract features comprising respiratory rates, inspiration and expiration from the trachea data set;

utilizing a computing device to extract features comprising heartbeat rate and abnormal heartbeat patterns from the heart data set;

utilizing a computing device to extract features comprising wheeze, rhonchi, squawk, coarse crackle and fine crackle and corresponding frequencies from the lung data sets; and causing a computing device to utilize predefined disease criteria and the extracted features to determine a result, wherein the result comprises at least one of COPD, asthma, VCD, pneumonia, CHF, and IPF, wherein the signal conditioning circuit comprises:
a second order high pass filter stage for filtering the signals from the plurality of electronic stethoscopes;

an isolator amplifier stage for isolating DC voltage and amplifying and transmitting AC voltage of filtered signals received from the second order high pass filter stage;

a second order active low pass filter stage for filtering signals received from the isolator amplifier stage;

a third order active high pass filter stage for filtering signals received from the second order active low pass filter stage;

a non-inverting amplifier stage for amplifying the signals received from the third order active high pass filter stage; and a first order passive low pass filter stage for filtering signals received from the non-inverting amplifier stage.

9. The method of claim 8, wherein:
the predefined disease criteria for COPD comprises at least one of wheeze, rhonchi, inspiration-expiration ratio, high inspiration lag and lead time, high expiration time delay and abnormal respiratory rates.

10. The method of claim 9, wherein:
the predefined disease criteria for asthma comprises at least one of wheeze, rhonchi, low inspiration-expiration ratio, high expiration time delay and abnormal respiration rates, and wherein asthma is diagnosed if inspiration lag and lead time are not present in the data sets.

11. The method of claim 10, wherein:
the predefined disease criteria for VCD comprises at last one of a) wheeze, and b) highly symmetrical wheeze at both lungs, wherein a symmetry coefficient is utilized to determine if the wheeze meets predefined VCD symmetry criteria.

12. The method of claim 11, wherein:
the predefined disease criteria for pneumonia comprises at least one of a) coarse crackles, b) rhonchi, c) squawk, and d) abnormal respiratory rate, wherein coarse crackles are determined to be present if discontinuous adventitious lung sounds with low frequency are detected in one or more of the data sets, and wherein squawks are determined to be present if short duration wheeze having quick sinusoidal waveform is detected in one or more of the data sets.

13. The method of claim 12, wherein:
the predefined disease criteria for CHF comprises at least one of a) coarse crackle, b) irregular heartbeat, and c) abnormal respiration rates, wherein the irregular heartbeat includes a rapid heartbeat rate and an abnormal heartbeat pattern.

14. The method of claim 13, wherein:
the predefined disease criteria for IPF comprises at least one of a) fine crackles, b) low crackle transmission coefficient, c) abnormal respiration rates, and d) a discontinuous adventitious lung sound with high frequency at the bases of the lungs.

15. The method of claim 9, wherein:
the predefined COPD criteria comprises a) an inspiration-expiration ratio below about 0.7, and b) an inspiration lag and lead time greater than about 3 ms, and c) an expiration time delay greater than about 3 ms, and d) respiratory rates that are less than about 12 breaths per minute or greater than about 25 breaths per minute.

16. The method of claim 10, wherein:
the predefined asthma criteria comprises a) an inspiration-expiration ratio below about 0.7, and b) an expiration time delay greater than about 3 ms, and c) respiratory rates less than about 12 breaths per minute or greater than about 25 breaths per minute.

17. The method of claim 11, wherein:
the predefined VCD symmetry criteria comprises a symmetry coefficient equal to or greater than about 0.5.

18. The method of claim 12, including:
utilizing a predefined pneumonia criteria comprising respiratory rates less than about 12 breaths per minute or greater than about 25 breaths per minute;
utilizing a coarse crackles criteria comprising discontinuous adventitious lung sounds having a frequency equal to or less than about 333 Hz; and
utilizing a squawk criteria comprising wheeze of equal to or less than about 100 ms.

19. The method of claim 13, including:
determining that coarse crackle is detected utilizing predefined criteria comprising discontinuous adventitious lung sounds having a frequency equal to or less than about 333 Hz are present;
determining that an abnormal respiration rate is detected utilizing predefined criteria comprising a) respiration rates less than about 12 breaths per minute, or b) respiration rates above about 25 breaths per minute; and
determining that a rapid heartbeat is detected utilizing predefined criteria comprising a heartbeat rate equal to or above about 100 beats per minute is detected.

20. The method of claim 14, wherein:
determining that fine crackles are detected utilizing predefined criteria comprising crackles having a frequency equal to or greater than about 333 Hz; and
determining that an abnormal respiration rate is detected utilizing predefined criteria comprising respiration rates less than about 12 breaths per minute or respiration rates above about 25 breaths per minute are detected.

* * * * *